(12) United States Patent
Chi et al.

(10) Patent No.: US 10,497,470 B2
(45) Date of Patent: Dec. 3, 2019

(54) MOBILE TERMINAL AND CONTROLLING METHOD THEREOF

(71) Applicant: LG ELECTRONICS INC., Seoul (KR)

(72) Inventors: Jumin Chi, Seoul (KR); Gukchan Lim, Seoul (KR); Hongjo Shim, Seoul (KR); Sanghyun Eim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 896 days.

(21) Appl. No.: 14/810,000

(22) Filed: Jul. 27, 2015

(65) Prior Publication Data

US 2016/0292365 A1 Oct. 6, 2016

(30) Foreign Application Priority Data

Apr. 1, 2015 (KR) .................. 10-2015-0045967

(51) Int. Cl.
| | |
|---|---|
| *G16H 50/30* | (2018.01) |
| *G16H 10/65* | (2018.01) |
| *A61B 5/00* | (2006.01) |
| *G06F 1/16* | (2006.01) |
| *G06F 3/01* | (2006.01) |
| *H04L 29/08* | (2006.01) |

(Continued)

(52) U.S. Cl.
CPC .......... *G16H 10/65* (2018.01); *A61B 5/681* (2013.01); *G06F 1/163* (2013.01); *G06F 3/016* (2013.01); *G16H 40/63* (2018.01); *H04L 67/12* (2013.01); *G06F 19/3481* (2013.01); *G16H 10/60* (2018.01); *G16H 15/00* (2018.01)

(58) Field of Classification Search
CPC ................ G16H 50/20; G06F 19/00
See application file for complete search history.

(56) References Cited

U.S. PATENT DOCUMENTS

| | | | |
|---|---|---|---|
| 2008/0146892 A1 | 6/2008 | Leboeuf et al. | |
| 2011/0098112 A1* | 4/2011 | LeBoeuf | G06F 19/00 463/31 |

FOREIGN PATENT DOCUMENTS

| | | |
|---|---|---|
| CN | 102178511 A | 9/2011 |
| CN | 103529684 A | 1/2014 |

(Continued)

*Primary Examiner* — John A Pauls
(74) *Attorney, Agent, or Firm* — Birch, Stewart, Kolasch & Birch, LLP

(57) ABSTRACT

A mobile terminal including a memory configured to store at least one of first information on a disease history of a preset user and second information on a preset disease; a wireless communication unit configured to receive information obtained through a sensor of a preset external device, wherein the received information comprises at least one of third information obtained from sensing a surrounding environment of the preset external device and fourth information obtained from sensing a current state of the preset user; a display unit; and a controller configured to determine a current health-related state of the preset user using at least one of the first information, the second information and the received information, determine a cause of the current health-related state of the preset user using at least one of the first information, the second information and the received information, and output information about the determined cause of the current health-related state of the preset user.

14 Claims, 24 Drawing Sheets

(51) Int. Cl.
*G16H 40/63* (2018.01)
*G06F 19/00* (2018.01)
*G16H 10/60* (2018.01)
*G16H 15/00* (2018.01)

(56) References Cited

FOREIGN PATENT DOCUMENTS

| | | |
|---|---|---|
| CN | 103957777 A | 7/2014 |
| WO | WO 2012/171032 A2 | 12/2012 |
| WO | WO 2013/086363 A2 | 6/2013 |

\* cited by examiner (a)  (b)

Figure 22
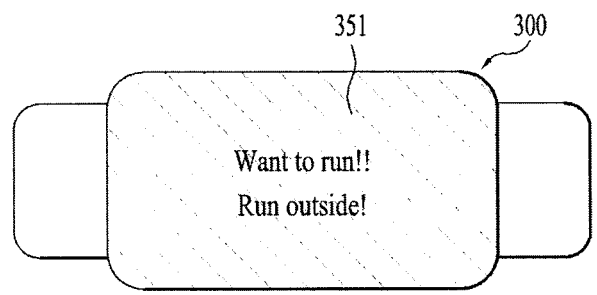
(a)
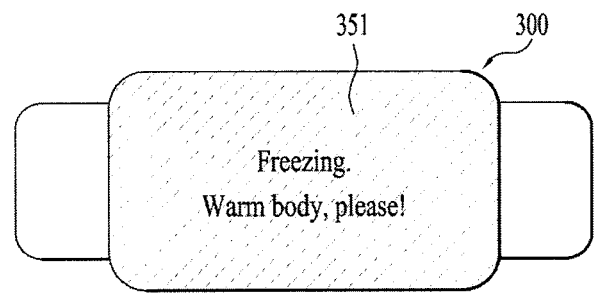
(b)
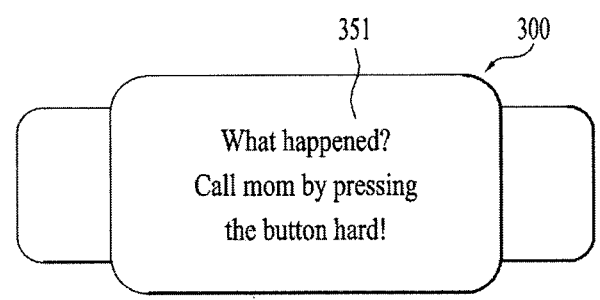
(c)

MOBILE TERMINAL AND CONTROLLING METHOD THEREOF

Pursuant to 35 U.S.C. § 119(a), this application claims the benefit of earlier filing date and right of priority to Korean Application No. 10-2015-0045967, filed on Apr. 1, 2015, the contents of which are hereby incorporated by reference herein in their entirety.

BACKGROUND OF THE INVENTION

Field of the Invention

The present invention relates to a mobile terminal, and more particularly, to a mobile terminal and controlling method thereof. Although the present invention is suitable for a wide scope of applications, it is particularly suitable for facilitating the use of a terminal in further consideration of user's convenience.

Discussion of the Related Art

Terminals may be generally classified as mobile/portable terminals or stationary terminals. Mobile terminals may also be classified as handheld terminals or vehicle mounted terminals. Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

The recent tendency of a mobile terminal market attempts to develop mobile terminals of various types to meet the diversity of the consumer's needs. The types of the developed mobile terminals are focused on the configuration that can emphasize the portability of the mobile terminal. The mobile terminal types for high portability can include such a type wearable on a user's body as a watch type, a glasses type, a necklace type and the like. Moreover, since these types of the mobile terminals are provided with various kinds of sensors, the user's health can be checked. However, the wearable type mobile terminal only obtains information about the user's health and then provides the obtained information to the user.

SUMMARY OF THE INVENTION

Accordingly, an object of the present invention is to address the above-noted and other problems.

One object of the present invention is to provide a mobile terminal and controlling method thereof, by which a user's current state of a preset external device can be easily removed by recognizing the user's current state of the preset external device and then extracting a cause of the recognized current state.

Another object of the present invention is to provide a mobile terminal and controlling method thereof, by which preset data can be output through an output unit. In particular, a mobile terminal of a wearable type sends information obtained through a sensing unit to a preset external device. If at least one value of the obtained information deviates from a range of a preset value, the preset data is output through the output unit.

Technical tasks obtainable from the present invention are non-limited by the above-mentioned technical tasks. And, other unmentioned technical tasks can be clearly understood from the following description by those having ordinary skill in the technical field to which the present invention pertains.

Additional advantages, objects, and features of the invention will be set forth in the disclosure herein as well as the accompanying drawings. Such aspects may also be appreciated by those skilled in the art based on the disclosure herein.

To achieve these objects and other advantages and in accordance with the purpose of the invention, as embodied and broadly described herein, a mobile terminal according to one embodiment of the present invention includes a memory configured to store at least one of first information on a disease history of a preset user and second information on a preset disease, a wireless communication unit configured to receive information obtained through a sensor of a preset external device, and a controller, wherein the received information comprises at least one of third information obtained from sensing a surrounding environment of the preset external device and fourth information obtained from sensing a state of the preset user, wherein the controller recognizes a current state of the preset user using at least one of the first information, the second information and the received information, and wherein the controller extracts a cause of the recognized current state of the preset user using at least one of the first information, the second information and the received information.

In another aspect of the present invention, as embodied and broadly described herein, a mobile terminal of a wearable type according to another embodiment of the present invention may include a sensing unit configured to obtain at least one of first information on a surrounding environment of the mobile terminal and second information on a state of a user of the mobile terminal, a wireless communication unit configured to transmit at least one of the obtained first information and the obtained second information to a preset external device, an output unit configured to output at least one of audio data, text data, optical data, video data, graphic data, and vibration data, and a controller, if a value of at least one of the first information and the second information deviates from a range of a preset first value, outputting a preset first data through the output unit.

In another aspect of the present invention, as embodied and broadly described herein, a method of controlling a mobile terminal according to another embodiment of the present invention may include the steps of saving at least one of first information on a disease history of a preset user and second information on a preset disease, receiving information including at least one of third information obtained from sensing a surrounding environment of a preset external device and fourth information obtained from sensing a state of the preset user, recognizing a current state of the preset user using at least one of the first information, the second information and the received information, and extracting a cause of the recognized current state of the preset user using at least one of the first information, the second information and the received information.

In further aspect of the present invention, as embodied and broadly described herein, a method of controlling a mobile terminal of a wearable type according to further embodiment of the present invention includes the steps of obtaining at least one of first information on a surrounding environment of the mobile terminal and second information on a state of a user of the mobile terminal, transmitting at least one of the obtained first information and the obtained second information to a preset external device, and if a value of at least one of the first information and the second information deviates from a range of a preset first value, outputting a preset first data.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

Effects obtainable from the present invention are non-limited by the above mentioned effect. And, other unmentioned effects can be clearly understood from the following description by those having ordinary skill in the technical field to which the present invention pertains.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 22 is a diagram illustrating another example of a method of outputting a different data depending on a value of at least one of information on a surrounding environment and information on a user's state in a mobile terminal according to one embodiment of the present invention;

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Although the terms first, second, etc. may be used herein to describe various elements, these elements should not be limited by these terms. These terms are generally only used to distinguish one element from another. When an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like. By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1A:
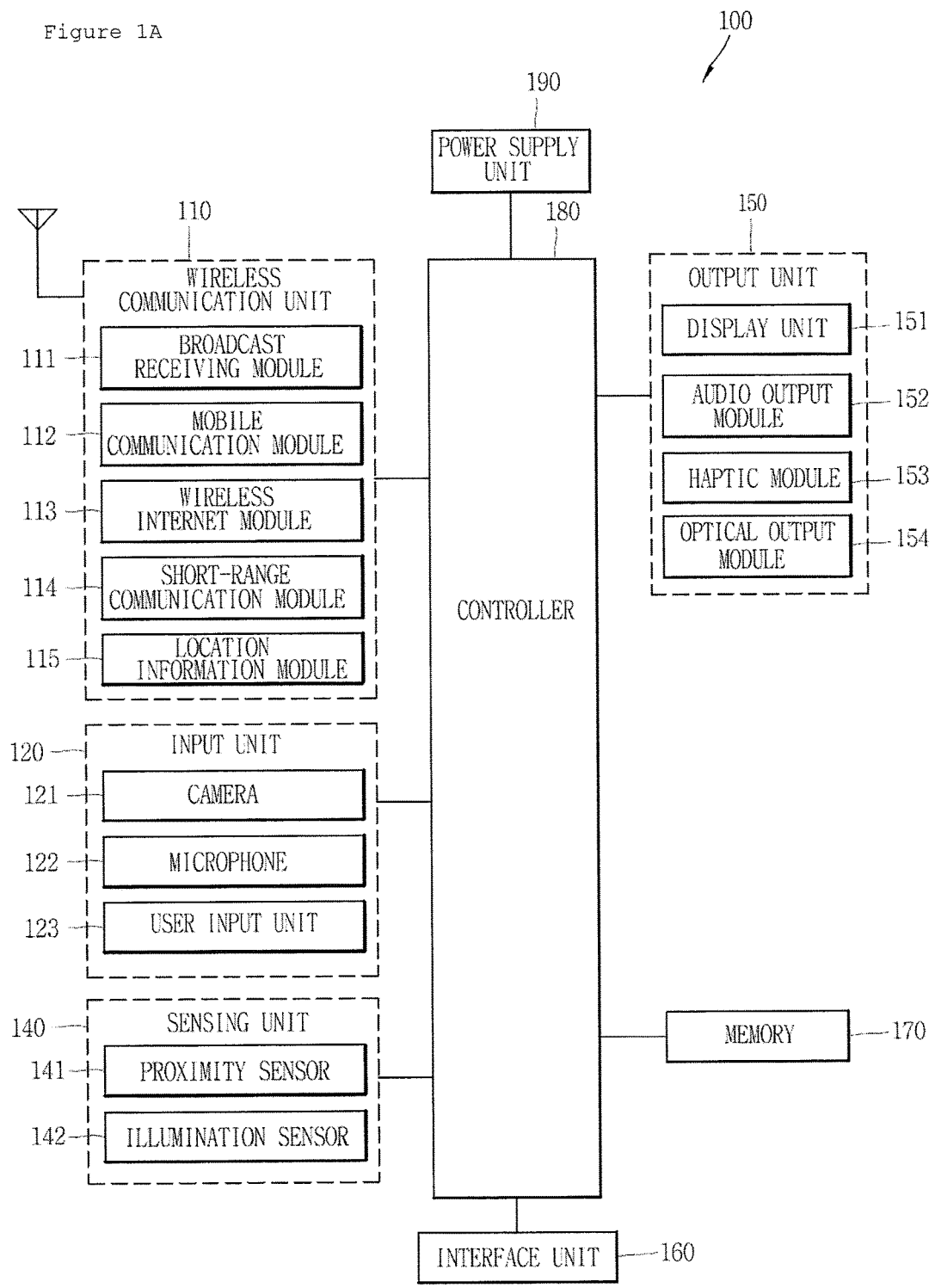
FIG. 1A is a block diagram of a mobile terminal in accordance with the present disclosure.
Figure 1B:
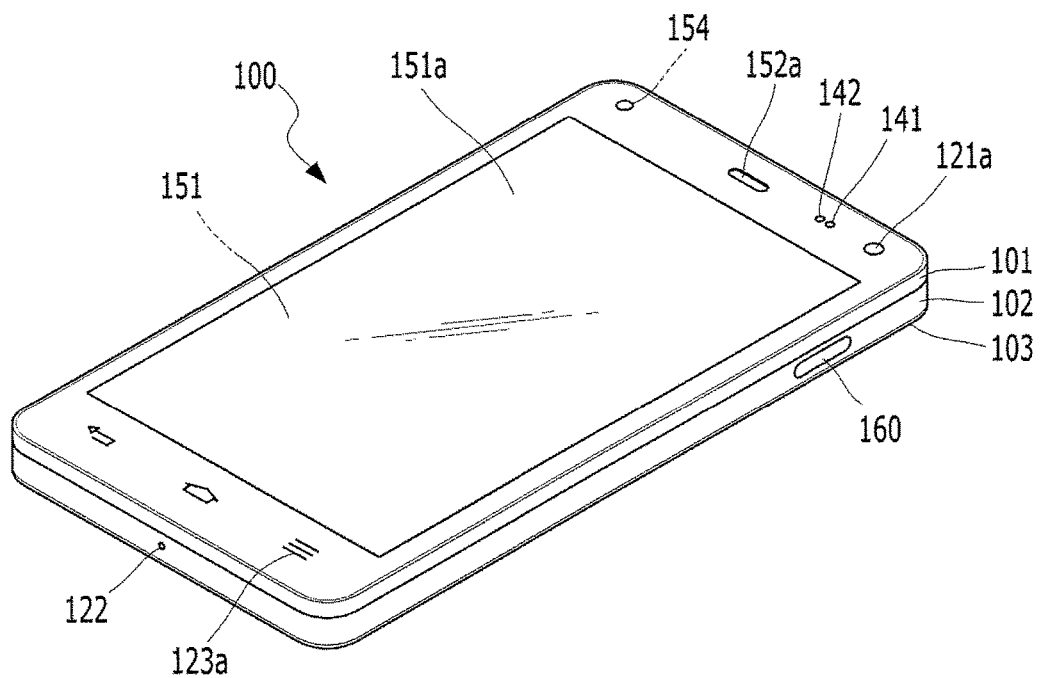
FIGS. 1B and 1C are conceptual views of one example of the mobile terminal, viewed from different directions.
Figure 1C:
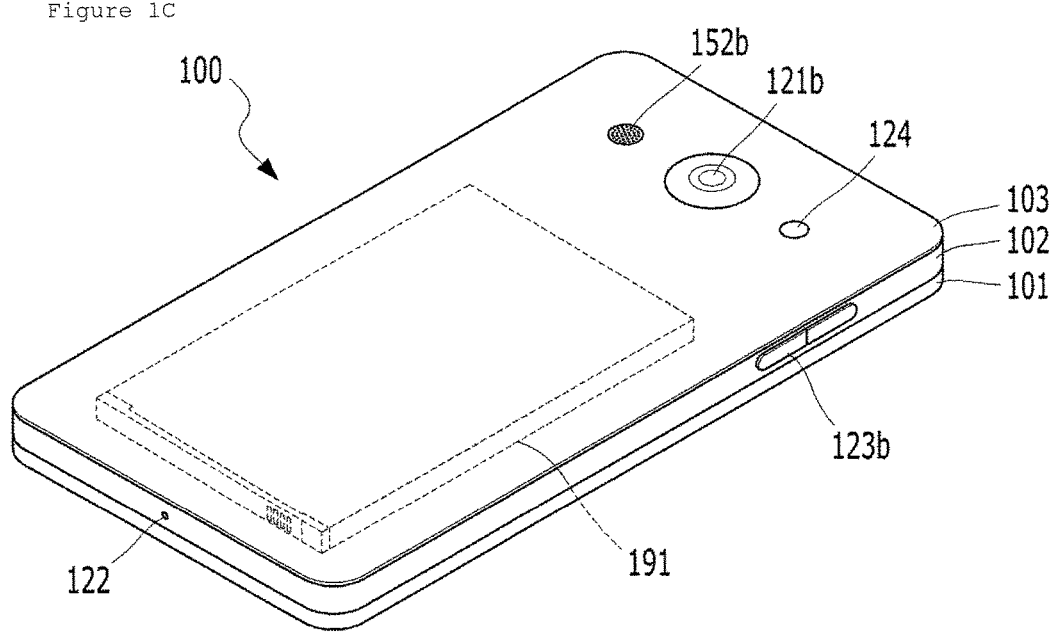

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions. The mobile terminal 100 is shown having components such as a wireless communication unit 110, an input unit 120, a sensing unit 140, an output unit 150, an interface unit 160, a memory 170, a controller 180, and a power supply unit 190. Implementing all of the illustrated components is not a requirement, and that greater or fewer components may alternatively be implemented.

Referring now to FIG. 1A, the mobile terminal 100 is shown having wireless communication unit 110 configured with several commonly implemented components. The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 (e.g., a microprocessor having sufficient structure and the appropriate algorithms) typically functions to control overall operation of the mobile terminal 100, in addition to the operations associated with the application programs. The controller 180 processes signals, data, information and the like input or output through the above-mentioned components and/or runs application programs saved in the memory 170, thereby processing or providing a user with appropriate information and/or functions.

The controller 180 can provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least one portion of the respective components mentioned in the foregoing description can cooperatively operate to embody operations, controls or controlling methods of the mobile terminal according to various embodiments of the present invention mentioned in the following description. Moreover, the operations, controls or controlling methods of the mobile terminal can be embodied in the mobile terminal by executing at least one or more application programs saved in the memory 170.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The broadcast managing entity may be implemented using a server or system which generates and transmits a broadcast signal and/or broadcast associated information, or a server which receives a pre-generated broadcast signal and/or broadcast associated information, and sends such items to the mobile terminal. The broadcast signal may be implemented using any of a TV broadcast signal, a radio broadcast signal, a data broadcast signal, and combinations thereof, among others. The broadcast signal in some cases may further include a data broadcast signal combined with a TV or radio broadcast signal.

The broadcast signal may be encoded according to any of a variety of technical standards or broadcasting methods (for example, International Organization for Standardization (ISO), International Electrotechnical Commission (IEC), Digital Video Broadcast (DVB), Advanced Television Systems Committee (ATSC), and the like) for transmission and reception of digital broadcast signals. The broadcast receiving module 111 can receive the digital broadcast signals using a method appropriate for the transmission method utilized.

Examples of broadcast associated information may include information associated with a broadcast channel, a broadcast program, a broadcast event, a broadcast service provider, or the like. The broadcast associated information may also be provided via a mobile communication network, and in this instance, received by the mobile communication module 112. The broadcast associated information may be implemented in various formats. For instance, broadcast associated information may include an Electronic Program Guide (EPG) of Digital Multimedia Broadcasting (DMB), an Electronic Service Guide (ESG) of Digital Video Broadcast-Handheld (DVB-H), and the like. Broadcast signals and/or broadcast associated information received via the broadcast receiving module 111 may be stored in a suitable device, such as a memory 170.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies. Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which can exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. Further, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this instance, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others. As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 can sense which region of the display unit 151 has been touched. Here, the touch controller may be a component separate from the controller 180, the controller 180, and combinations thereof.

In some embodiments, the controller 180 can execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like. If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor. Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information. In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

In general, a 3D stereoscopic image may include a left image (e.g., a left eye image) and a right image (e.g., a right eye image). According to how left and right images are combined into a 3D stereoscopic image, a 3D stereoscopic imaging method can be divided into a top-down method in which left and right images are located up and down in a frame, an L-to-R (left-to-right or side by side) method in which left and right images are located left and right in a frame, a checker board method in which fragments of left and right images are located in a tile form, an interlaced method in which left and right images are alternately located by columns or rows, and a time sequential (or frame by frame) method in which left and right images are alternately displayed on a time basis.

Also, as for a 3D thumbnail image, a left image thumbnail and a right image thumbnail can be generated from a left image and a right image of an original image frame, respectively, and then combined to generate a single 3D thumbnail image. In general, the term "thumbnail" may be used to refer to a reduced image or a reduced still image. A generated left image thumbnail and right image thumbnail may be displayed with a horizontal distance difference there between by a depth corresponding to the disparity between the left image and the right image on the screen, thereby providing a stereoscopic space sense.

A left image and a right image required for implementing a 3D stereoscopic image may be displayed on the stereoscopic display unit using a stereoscopic processing unit. The stereoscopic processing unit can receive the 3D image and extract the left image and the right image, or can receive the 2D image and change it into a left image and a right image.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like. The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like. A signal output by the optical output module 154 may be implemented so the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen. The memory 170 may include one or more types of storage mediums including a Flash memory, a hard disk, a solid state disk, a silicon disk, a multimedia card micro type, a card-type memory (e.g., SD or DX memory, etc.), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 can typically control the general operations of the mobile terminal 100. For example, the controller 180 can set or release a lock state for restricting a user from inputting a control command with respect to applications when a status of the mobile terminal meets a preset condition. The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging. The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance. Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations.

Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151*a* of the display unit 151 may be mounted to the front case 101 to form the front surface of the terminal body together with the front case 101. In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121*b* or an audio output module 152*b*.

The cases 101, 102, 103 may be formed by injection-molding synthetic resin or may be formed of a metal, for example, stainless steel (STS), aluminum (Al), titanium (Ti), or the like. As an alternative to the example in which the plurality of cases form an inner space for accommodating components, the mobile terminal 100 may be configured such that one case forms the inner space. In this example, a mobile terminal 100 having a uni-body is formed so synthetic resin or metal extends from a side surface to a rear surface.

If desired, the mobile terminal 100 may include a waterproofing unit for preventing introduction of water into the terminal body. For example, the waterproofing unit may include a waterproofing member which is located between the window 151*a* and the front case 101, between the front case 101 and the rear case 102, or between the rear case 102 and the rear cover 103, to hermetically seal an inner space when those cases are coupled.

The mobile terminal 100 may be provided with the display unit 151, the first audio output unit 152*a*, the second audio output unit 152*b*, the proximity sensor 141, the illumination sensor 142, the optical output unit 154, the first camera 121*a*, the second camera 121*b*, the first manipulating unit 123*a*, the second manipulating unit 123*b*, the microphone 122, the interface unit 160, and the like.

FIGS. 1B and 1C depict certain components as arranged on the mobile terminal. However, alternative arrangements are possible and within the teachings of the instant disclosure. Some components may be omitted or rearranged. For example, the first manipulation unit 123*a* may be located on another surface of the terminal body, and the second audio output module 152*b* may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof. The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151*a* and a display on a rear surface of the window 151*a*, or a metal wire which is patterned directly on the rear surface of the window 151*a*. Alternatively, the touch sensor may be integrally formed with the display. For example, the touch sensor may be disposed on a substrate of the display or within the display. The display unit 151 may also form a touch screen together with the touch sensor. Here, the touch screen may serve as the user input unit 123 (see FIG. 1A). Therefore, the touch screen may replace at least some of the functions of the first manipulation unit 123*a*.

The first audio output module 152*a* may be implemented in the form of a speaker to output voice audio, alarm sounds, multimedia audio reproduction, and the like. The window 151*a* of the display unit 151 will typically include an aperture to permit audio generated by the first audio output module 152*a* to pass. One alternative is to allow audio to be released along an assembly gap between the structural bodies (for example, a gap between the window 151*a* and the front case 101). In this instance, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output. The first camera 121*a* can process image frames such as still or moving images obtained by the image sensor in a capture mode or a video call mode. The processed image frames can then be displayed on the display unit 151 or stored in the memory 170.

The first and second manipulation units 123*a* and 123*b* are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof. Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen. As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject. As shown in FIG. 1C, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

Meanwhile, according to an embodiment of the present invention, the mobile terminal can display information processed by the mobile terminal using a flexible display. This is described in detail with reference to the accompanying drawings as follows.

Figure 2:
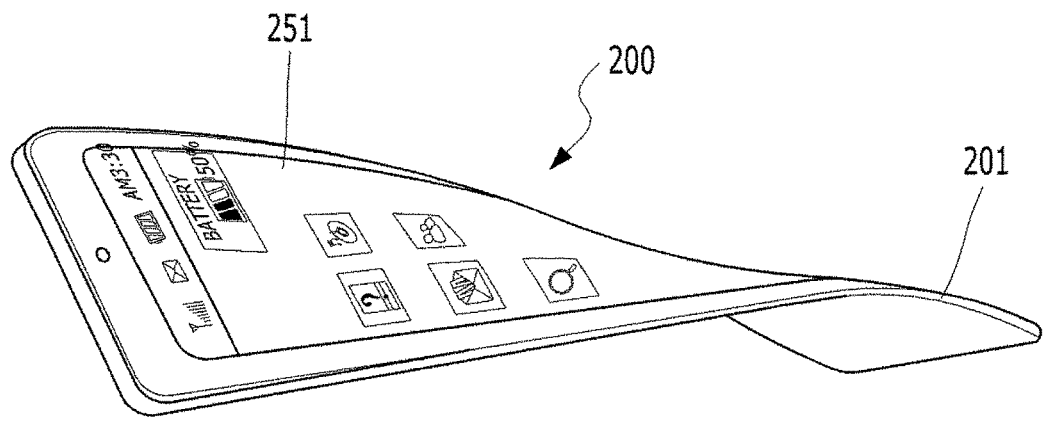
FIG. 2 is a conceptual view of a deformable mobile terminal according to an alternative embodiment of the present disclosure.

FIG. 2 is a conceptual view of a deformable mobile terminal according to an alternative embodiment of the present invention. In this figure, mobile terminal 200 is shown having display unit 251, which is a type of display that is deformable by an external force. This deformation, which includes display unit 251 and other components of mobile terminal 200, may include any of curving, bending, folding, twisting, rolling, and combinations thereof. The deformable display unit 251 may also be referred to as a "flexible display unit." In some implementations, the flexible display unit 251 may include a general flexible display, electronic paper (also known as e-paper), and combinations thereof. In general, mobile terminal 200 may be configured to include features that are the same or similar to that of mobile terminal 100 of FIGS. 1A-1C.

The flexible display of mobile terminal 200 is generally formed as a lightweight, non-fragile display, which still exhibits characteristics of a conventional flat panel display, but is instead fabricated on a flexible substrate which can be deformed as noted previously. The term e-paper may be used to refer to a display technology employing the characteristic of a general ink, and is different from the conventional flat panel display in view of using reflected light. E-paper is generally understood as changing displayed information using a twist ball or via electrophoresis using a capsule.

When the flexible display unit 251 is not deformed (for example, in a state with an infinite radius of curvature and referred to as a first state), a display region of the flexible display unit 251 includes a generally flat surface. When the flexible display unit 251 is deformed from the first state by an external force (for example, a state with a finite radius of curvature and referred to as a second state), the display region may become a curved surface or a bent surface. As illustrated, information displayed in the second state may be visual information output on the curved surface. The visual information may be realized so a light emission of each unit pixel (sub-pixel) arranged in a matrix configuration is controlled independently. The unit pixel denotes an elementary unit for representing one color.

According to one alternative embodiment, the first state of the flexible display unit 251 may be a curved state (for example, a state of being curved from up to down or from right to left), instead of being in flat state. In this embodiment, when an external force is applied to the flexible display unit 251, the flexible display unit 251 may transition to the second state such that the flexible display unit is deformed into the flat state (or a less curved state) or into a more curved state.

If desired, the flexible display unit 251 may implement a flexible touch screen using a touch sensor in combination with the display. When a touch is received at the flexible touch screen, the controller 180 can execute certain control corresponding to the touch input. In general, the flexible touch screen is configured to sense touch and other input while in both the first and second states. One option is to configure the mobile terminal 200 to include a deformation sensor which senses the deforming of the flexible display unit 251. The deformation sensor may be included in the sensing unit 140.

The deformation sensor may be located in the flexible display unit 251 or the case 201 to sense information related to the deforming of the flexible display unit 251. Examples of such information related to the deforming of the flexible display unit 251 may be a deformed direction, a deformed degree, a deformed position, a deformed amount of time, an acceleration that the deformed flexible display unit 251 is restored, and the like. Other possibilities include most any type of information which can be sensed in response to the curving of the flexible display unit or sensed while the flexible display unit 251 is transitioning into, or existing in, the first and second states.

In some embodiments, controller 180 or other component can change information displayed on the flexible display unit 251, or generate a control signal for controlling a function of the mobile terminal 200, based on the information related to the deforming of the flexible display unit 251. Such information is typically sensed by the deformation sensor. The mobile terminal 200 is shown having a case 201 for accommodating the flexible display unit 251. The case 201 can be deformable together with the flexible display unit 251, taking into account the characteristics of the flexible display unit 251.

A battery located in the mobile terminal 200 may also be deformable in cooperation with the flexible display unit 261, taking into account the characteristic of the flexible display unit 251. One technique to implement such a battery is to use a stack and folding method of stacking battery cells. The deformation of the flexible display unit 251 not limited to perform by an external force. For example, the flexible display unit 251 can be deformed into the second state from the first state by a user command, application command, or the like.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like. A typical wearable device can exchange data with (or cooperate with) another mobile terminal 100. In such a device, the wearable device generally has functionality that is less than the cooperating mobile terminal.

For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 can transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 3:
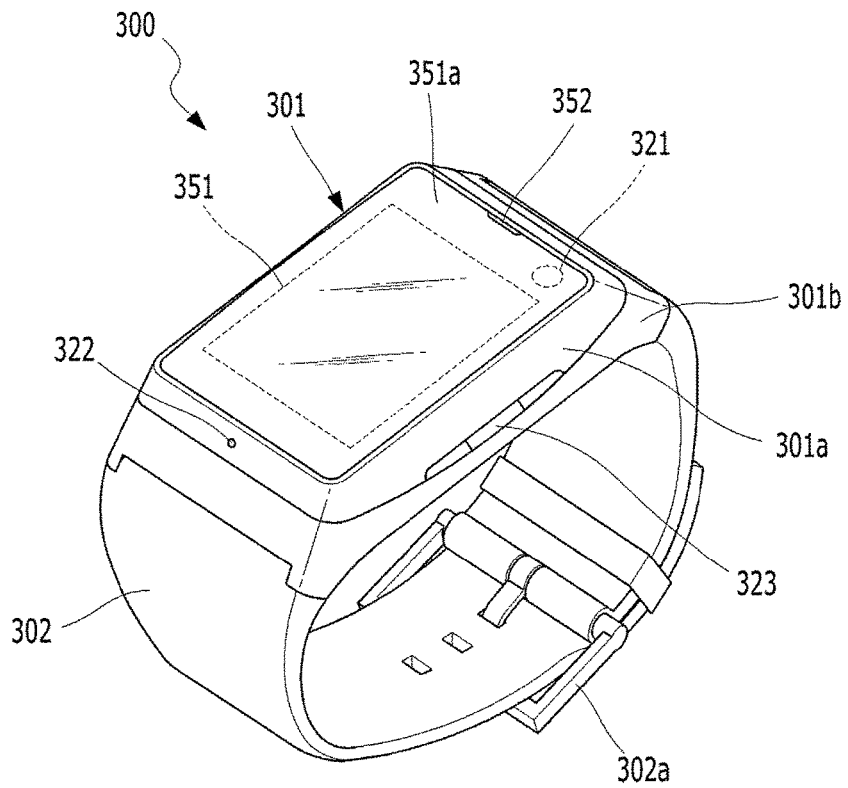
FIG. 3 is a conceptual view of a wearable mobile terminal according to another alternative embodiment of the present disclosure.

FIG. 3 is a perspective view illustrating one example of a watch-type mobile terminal 300 in accordance with another exemplary embodiment. As illustrated in FIG. 3, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1A-1C.

The main body 301 includes a case having a certain appearance. As illustrated, the case includes a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion electrically connected to the antenna to extend a ground area. The band 302 includes fastener 302a. The fastener 302a may be implemented into a buckle type, a snap-fit hook structure, a Velcro® type, or the like, and include a flexible section or material. The drawing illustrates an example that the fastener 302a is implemented using a buckle.

Figure 4:
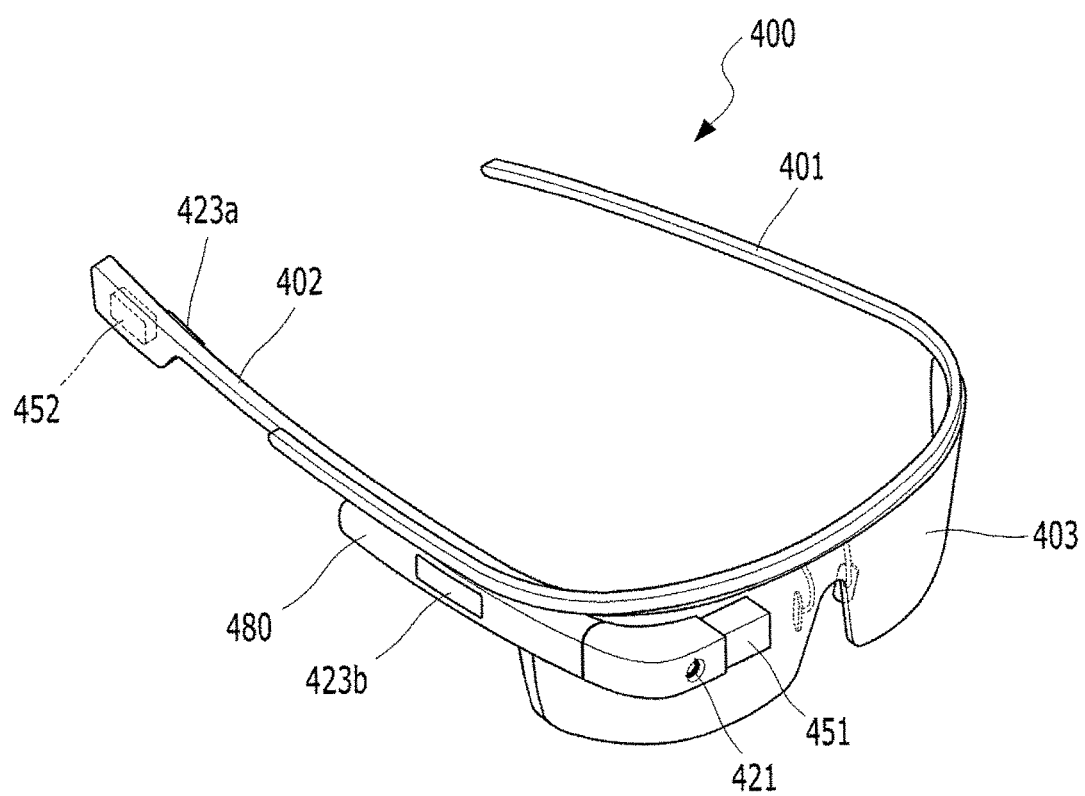
FIG. 4 is a conceptual view of a wearable mobile terminal according to another alternative embodiment of the present disclosure.

FIG. 4 is a perspective view illustrating one example of a glass-type mobile terminal 400 according to another exemplary embodiment. The glass-type mobile terminal 400 can be wearable on a head of a human body and provided with a frame (case, housing, etc.) therefor. The frame may be made of a flexible material to be easily worn. The frame of mobile terminal 400 is shown having a first frame 401 and a second frame 402, which can be made of the same or different materials. In general, mobile terminal 400 may be configured to include features that are the same or similar to that of mobile terminal 100 of FIGS. 1A-1C.

The frame may be supported on the head and defines a space for mounting various components. As illustrated, electronic components, such as a control module 480, an audio output module 452, and the like, may be mounted to the frame part. Also, a lens 403 for covering either or both of the left and right eyes may be detachably coupled to the frame part. The control module 480 controls various electronic components disposed in the mobile terminal 400. The control module 480 may be understood as a component corresponding to the aforementioned controller 180. FIG. 4 illustrates that the control module 480 is installed in the frame part on one side of the head, but other locations are possible.

The display unit 451 may be implemented as a head mounted display (HMD). The HMD refers to display techniques by which a display is mounted to a head to show an image directly in front of a user's eyes. In order to provide an image directly in front of the user's eyes when the user wears the glass-type mobile terminal 400, the display unit 451 may be located to correspond to either or both of the left and right eyes. FIG. 4 illustrates that the display unit 451 is located on a portion corresponding to the right eye to output an image viewable by the user's right eye.

The display unit 451 may project an image into the user's eye using a prism. Also, the prism may be formed from optically transparent material such that the user can view both the projected image and a general visual field (a range that the user views through the eyes) in front of the user. In such a manner, the image output through the display unit 451 may be viewed while overlapping with the general visual field. The mobile terminal 400 may provide an augmented reality (AR) by overlaying a virtual image on a realistic image or background using the display.

The camera 421 may be located adjacent to either or both of the left and right eyes to capture an image. Since the camera 421 is located adjacent to the eye, the camera 421 can acquire a scene that the user is currently viewing. The camera 421 may be positioned at most any location of the mobile terminal. In some embodiments, multiple cameras 421 may be utilized. Such multiple cameras 421 may be used to acquire a stereoscopic image.

The glass-type mobile terminal 400 includes user input units 423a and 423b, which can each be manipulated by the user to provide an input. The user input units 423a and 423b may employ techniques which permit input via a tactile input. Typical tactile inputs include a touch, push, or the like. The user input units 423a and 423b are shown operable in a pushing manner and a touching manner as they are located on the frame part and the control module 480, respectively.

If desired, the mobile terminal 400 may include a microphone which processes input sound into electric audio data, and an audio output module 452 for outputting audio. The audio output module 452 may be configured to produce audio in a general audio output manner or an osteoconductive manner. When the audio output module 452 is implemented in the osteoconductive manner, the audio output module 452 may be closely adhered to the head when the user wears the mobile terminal 400 and vibrate the user's skull to transfer sounds.

A communication system which is operable with the variously described mobile terminals will now be described in more detail. Such a communication system may be configured to utilize any of a variety of different air interfaces and/or physical layers. Examples of such air interfaces utilized by the communication system include Frequency Division Multiple Access (FDMA), Time Division Multiple Access (TDMA), Code Division Multiple Access (CDMA), Universal Mobile Telecommunications System (UMTS) (including, Long Term Evolution (LTE), LTE-A (Long Term Evolution-Advanced)), Global System for Mobile Communications (GSM), and the like.

By way of a non-limiting example only, further description will relate to a CDMA communication system, but such teachings apply equally to other system types including a CDMA wireless communication system as well as OFDM (Orthogonal Frequency Division Multiplexing) wireless communication system. A CDMA wireless communication system generally includes one or more mobile terminals (MT or User Equipment, UE) 100, one or more base stations (BSs, NodeB, or evolved NodeB), one or more base station controllers (BSCs), and a mobile switching center (MSC). The MSC is configured to interface with a conventional Public Switched Telephone Network (PSTN) and the BSCs. The BSCs are coupled to the base stations via backhaul lines. The backhaul lines may be configured in accordance with any of several known interfaces including, for example, E1/T1, ATM, IP, PPP, Frame Relay, HDSL, ADSL, or xDSL. Hence, the plurality of BSCs can be included in the CDMA wireless communication system.

Each base station may include one or more sectors, each sector having an omni-directional antenna or an antenna pointed in a particular direction radially away from the base station. Alternatively, each sector may include two or more different antennas. Each base station may be configured to support a plurality of frequency assignments, with each frequency assignment having a particular spectrum (e.g., 1.25 MHz, 5 MHz, etc.).

The intersection of sector and frequency assignment may be referred to as a CDMA channel. The base stations may also be referred to as Base Station Transceiver Subsystems (BTSs). In some cases, the term "base station" may be used to refer collectively to a BSC, and one or more base stations. The base stations may also be denoted as "cell sites." Alternatively, individual sectors of a given base station may be referred to as cell sites. A broadcasting transmitter (BT) transmits a broadcast signal to the mobile terminals 100 operating within the system. The broadcast receiving module 111 of FIG. 1A is typically configured inside the mobile terminal 100 to receive broadcast signals transmitted by the BT.

Global Positioning System (GPS) satellites for locating the position of the mobile terminal 100, for example, may cooperate with the CDMA wireless communication system. Useful position information may be obtained with greater or fewer satellites than two satellites. It is to be appreciated that other types of position detection technology, (i.e., location technology that may be used in addition to or instead of GPS location technology) may alternatively be implemented. If desired, at least one of the GPS satellites may alternatively or additionally be configured to provide satellite DMB transmissions.

The location information module 115 is generally configured to detect, calculate, or otherwise identify a position of the mobile terminal. As an example, the location information module 115 may include a Global Position System (GPS) module, a Wi-Fi module, or both. If desired, the location information module 115 may alternatively or additionally function with any of the other modules of the wireless communication unit 110 to obtain data related to the position of the mobile terminal.

A typical GPS module 115 can measure an accurate time and distance from three or more satellites, and accurately calculate a current location of the mobile terminal according to trigonometry based on the measured time and distances. A method of acquiring distance and time information from three satellites and performing error correction with a single satellite may be used. In particular, the GPS module may acquire an accurate time together with three-dimensional speed information as well as the location of the latitude, longitude and altitude values from the location information received from the satellites.

Furthermore, the GPS module can acquire speed information in real time to calculate a current position. Sometimes, accuracy of a measured position may be compromised when the mobile terminal is located in a blind spot of satellite signals, such as being located in an indoor space. In order to minimize the effect of such blind spots, an alternative or supplemental location technique, such as Wi-Fi Positioning System (WPS), may be utilized.

The Wi-Fi positioning system (WPS) refers to a location determination technology based on a wireless local area network (WLAN) using Wi-Fi as a technology for tracking the location of the mobile terminal 100. This technology typically includes the use of a Wi-Fi module in the mobile terminal 100 and a wireless access point for communicating with the Wi-Fi module. The Wi-Fi positioning system may include a Wi-Fi location determination server, a mobile terminal, a wireless access point (AP) connected to the mobile terminal, and a database stored with wireless AP information.

The mobile terminal connected to the wireless AP may transmit a location information request message to the Wi-Fi location determination server. The Wi-Fi location determination server extracts the information of the wireless AP connected to the mobile terminal 100, based on the location information request message (or signal) of the mobile terminal 100. The information of the wireless AP may be transmitted to the Wi-Fi location determination server through the mobile terminal 100, or may be transmitted to the Wi-Fi location determination server from the wireless AP.

The information of the wireless AP extracted based on the location information request message of the mobile terminal 100 may include one or more of media access control (MAC) address, service set identification (SSID), received signal strength indicator (RSSI), reference signal received Power (RSRP), reference signal received quality (RSRQ), channel information, privacy, network type, signal strength, noise strength, and the like.

The Wi-Fi location determination server may receive the information of the wireless AP connected to the mobile terminal 100 as described above, and may extract wireless AP information corresponding to the wireless AP connected to the mobile terminal from the pre-established database. The information of any wireless APs stored in the database may be information such as MAC address, SSID, RSSI, channel information, privacy, network type, latitude and longitude coordinate, building at which the wireless AP is located, floor number, detailed indoor location information (GPS coordinate available), AP owner's address, phone number, and the like. In order to remove wireless APs provided using a mobile AP or an illegal MAC address during a location determining process, the Wi-Fi location determination server may extract only a predetermined number of wireless AP information in order of high RSSI.

Then, the Wi-Fi location determination server may extract (analyze) location information of the mobile terminal 100 using at least one wireless AP information extracted from the database. A method for extracting (analyzing) location information of the mobile terminal 100 may include a Cell-ID method, a fingerprint method, a trigonometry method, a landmark method, and the like.

The Cell-ID method is used to determine a position of a wireless AP having the largest signal strength, among peripheral wireless AP information collected by a mobile terminal, as a position of the mobile terminal. The Cell-ID method is an implementation that is minimally complex, does not require additional costs, and location information can be rapidly acquired. However, in the Cell-ID method, the precision of positioning may fall below a desired threshold when the installation density of wireless APs is low.

The fingerprint method is used to collect signal strength information by selecting a reference position from a service area, and to track a position of a mobile terminal using the signal strength information transmitted from the mobile terminal based on the collected information. In order to use the fingerprint method, it is common for the characteristics of radio signals to be pre-stored in the form of a database.

The trigonometry method is used to calculate a position of a mobile terminal based on a distance between coordinates of at least three wireless APs and the mobile terminal. In order to measure the distance between the mobile terminal and the wireless APs, signal strength may be converted into distance information, Time of Arrival (ToA), Time Difference of Arrival (TDoA), Angle of Arrival (AoA), or the like may be taken for transmitted wireless signals.

The landmark method is used to measure a position of a mobile terminal using a known landmark transmitter. In addition to these position location methods, various algorithms may be used to extract (analyze) location information of a mobile terminal. Such extracted location information may be transmitted to the mobile terminal 100 through the Wi-Fi location determination server, thereby acquiring location information of the mobile terminal 100.

The mobile terminal 100 can acquire location information by being connected to at least one wireless AP. The number of wireless APs required to acquire location information of the mobile terminal 100 may be variously changed according to a wireless communication environment within which the mobile terminal 100 is positioned.

As previously described with regard to FIG. 1A, the mobile terminal may be configured to include short-range communication techniques such as Bluetooth™, Radio Frequency Identification (RFID), Infrared Data Association (IrDA), Ultra Wideband (UWB), ZigBee, Near Field Communication (NFC), Wireless USB (Wireless Universal Serial Bus), and the like.

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium such as Universal Integrated Circuit Card (UICC) (e.g., a Subscriber Identification Module (SIM) or Universal SIM (USIM)), a secure micro SD and a sticker, or a logical medium (e.g., embedded Secure Element (SE)) embedded in the mobile terminal. Single Wire Protocol (SWP)-based data exchange may be performed between the NFC module and the security module.

When the NFC module operates in a card mode, the mobile terminal may transmit card information on a general IC card to the outside. More specifically, if a mobile terminal having card information on a payment card (e.g, a credit card or a bus card) approaches a card reader, a short-range mobile payment may be executed. As another example, if a mobile terminal which stores card information on an entrance card approaches an entrance card reader, an entrance approval procedure may start. A card such as a credit card, a traffic card, or an entrance card may be included in the security module in the form of applet, and the security module may store card information on the card mounted therein. Card information for a payment card may include any of a card number, a remaining amount and usage history, and the like. Card information of an entrance card may include any of a user's name, a user's number (e.g., undergraduate number or staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs) such as smart poster, text, Uniform Resource Identifier (URI), and general control. If the data received from the external tag is a smart poster type, the controller may execute a browser (e.g., Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in a P2P (Peer-to-Peer) mode, the mobile terminal can execute P2P communication with another mobile terminal. In this instance, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For a typical P2P communication, data such as an electronic type name card, address information, a digital photo and a URL, a setup parameter for Bluetooth connection, Wi-Fi connection, etc. may be switched. The P2P mode can be effectively utilized in switching data of a small capacity, because an available distance for NFC communication is relatively short.

Further preferred embodiments will be described in more detail with reference to additional drawing figures. It is understood by those skilled in the art that the present features can be embodied in several forms without departing from the characteristics thereof. In the following description, embodiments of the present invention shall be explained in detail by taking the former mobile terminal 100 shown in FIG. 1A as one example of a mobile terminal. Moreover, a mobile terminal according to one embodiment of the present invention can be embodied by one of the former mobile terminals 200, 300 and 400 shown I FIGS. 2 to 4.

Examples of a method of providing various kinds of information using at least one of information previously saved in the memory 170 and information received from a preset external device in the mobile terminal 100 according to one embodiment of the present invention shall be described in detail with reference to FIGS. 5 to 15.

First of all, the preset external device may mean an external device connected to the mobile terminal 100 by wireless communication on a preset condition as a device capable of transmitting a specific signal to the mobile terminal 100 or receiving a specific signal from the mobile terminal 100. A type of the preset external device may include one of a smartwatch, a smart class, an HMD (head mounted display), a headset, and the like.

The information previously saved in the memory 170 may include at least one of first information on a disease history of a user (hereinafter named a preset user) of the preset external device and second information on a preset disease. The first information may include at least one of information on a type of a disease caught by the preset user, information (e.g., information indicating that the preset user may catch a cold if a sleeping time is smaller than 4 hours, etc.) on a specific life pattern corresponding to a disease caught by the preset user, information (e.g., information indicating that the preset user caught a cold if a measured temperature deviates from a predetermined range, etc.) on a surrounding environment corresponding to a disease caught by the preset user, and information (e.g., information indicating that the preset user caught a cold if a body temperature of the preset user is measured into a specific temperature, etc.) on a state of the preset user corresponding to a disease caught by the preset user.

The second information may include at least one of information on an incubation period of a preset disease, information on a prevention method of the preset disease, and information on symptoms related to the preset disease. In this instance, the preset disease may include at least one of a disease frequently occurring in the preset user, a disease breaking out in a specific season, a disease currently occurring in the preset user, and a disease selected by a user of the mobile terminal 100.

The information received from the preset external device may include at least one of third information obtained from sensing a surrounding environment of the preset external device and fourth information obtained from sensing a state of the preset user. The third information is the information obtained from sensing a surrounding environment periodically or aperiodically through a sensor of the preset external device and may include at least one of information on an amount of dust around the preset external device, information on a current location, information on a quality of air, information on a surrounding temperature, information on a surrounding atmospheric pressure, and information on a surrounding humidity.

The fourth information is the information obtained from sensing a state of the preset user periodically or aperiodically through a sensor of the preset external device and may include at least one of information on respiration of the preset user, information on a quantity of sweat of the preset user, information on a motion of the preset user, information on a heart rate of the preset user, information on a body temperature of the preset user, and information on a skin temperature of the preset user. Using at least one of the first information, the second information, the third information and the fourth information, the controller 180 can recognize a current state of the preset user. Using at least one of the first information, the second information, the third information and the fourth information, the controller 180 can extract a cause of the recognized current state of the preset user.

The current state of the preset user may include at least one of a state that a specific disease (e.g., a sore throat, a sinus cold, etc.) has occurred in the preset user, a state that the preset user currently doing a specific thing (e.g., exercise, sleep, etc.), and a state corresponding to an emergency (e.g., a situation that the preset user currently sinks under the water, a situation that a heart rate of the preset user is abnormal, etc.) occurring in the preset user.

The cause of the current state of the preset user is the cause that the preset user is in the current state and may include at least one of a cause (e.g., a quantity of dust, a surrounding temperature, etc.) of a disease occurring in the preset user and a cause (e.g., a situation of sinking under the water, a heart attack, etc.) of an emergency of the preset user. The controller 180 can provide a user of the mobile terminal 100 with the recognized current state of the preset user and a cause of the current state. For instance, if the current state of the preset user is a state that the preset user is exercising, the controller 180 can provide at least one of information on calories consumed by the preset user, information on a time of the exercise done by the preset user, and information on an exercise amount during a preset period (e.g., 1 week, etc.).

In another instance, if the current state of the preset user is a sleep state, the controller 180 can provide information (e.g., information indicating whether apnea occurs during the sleep, information on the number of toss and turn during the sleep, etc.) on a quality of the preset user's sleep. In particular, in the mobile terminal 100 according to one embodiment of the present invention, the controller 180 recognizes a current state of a preset user using at least one of information saved in the memory 170 and information received from a preset external device and then extracts a cause of the recognized current state, thereby providing a user of the mobile terminal 100 with the current state of the preset user and the cause of the current state. The following description is made with reference to FIGS. 5 to 15 in consideration of the above-mentioned contents.

Figure 5:
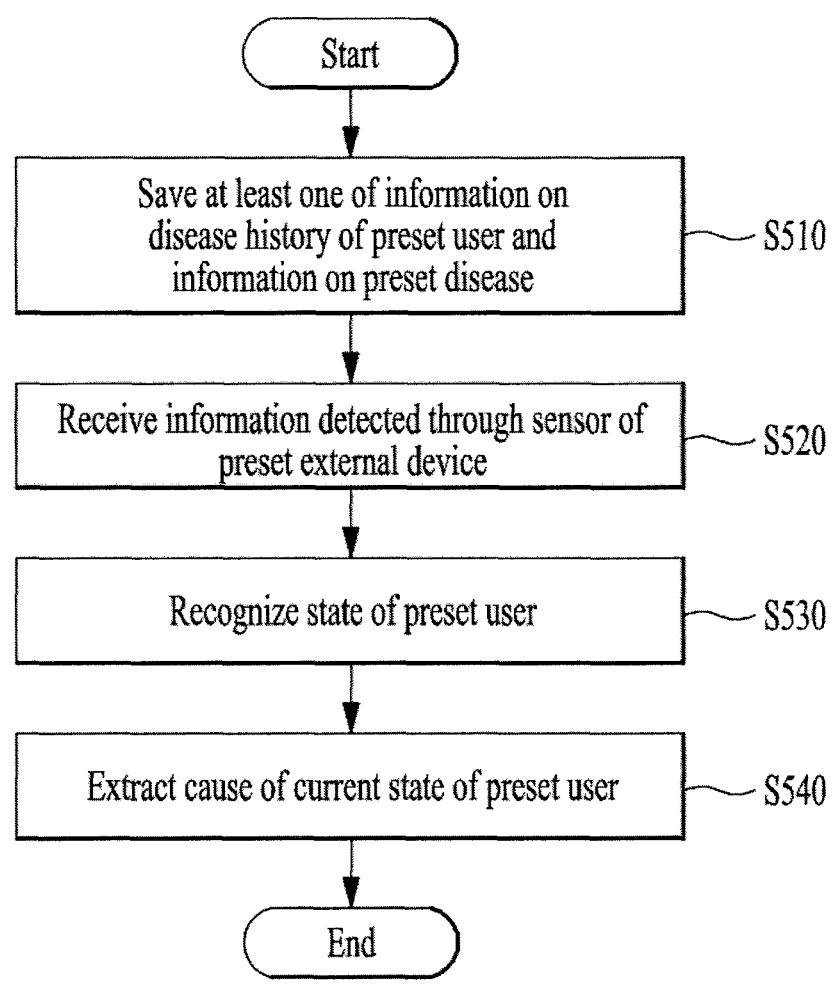
FIG. 5 is a flowchart illustrating one example of a method of extracting a cause of a current state by recognizing a user's current state of a preset external device in a mobile terminal according to one embodiment of the present invention.

In particular, FIG. 5 is a flowchart illustrating one example of a method of extracting a cause of a current state by recognizing a user's current state of a preset external device in a mobile terminal according to one embodiment of the present invention. Referring to FIG. 5, the memory 170 can currently store at least one of first information on a preset user's disease history and second information on a preset disease (S510). In this instance, the first information includes information input by a user of the mobile terminal 100, information saved by being received from the preset external device periodically or aperiodically, or information received from a specific external server (e.g., a hospital server, etc.) periodically or aperiodically. The second information includes information saved in the memory 170 before shipment, information saved in the memory 170 on upgrading a specific application (e.g., a child management application, etc.), information separately saved in the memory 170 by a user, or information received from a specific external server (e.g., a hospital server, etc.) periodically or aperiodically.

The controller 180 can control the wireless communication unit 110 to establish a wireless communication with a preset external device. In this instance, the wireless communication unit 110 includes at least one of the mobile communication module 112, the short range communication module 114, the wireless internet module 113, and the like. For instance, if a command for establishing the wireless communication with the preset external device is detected or a specific signal for establishing the wireless communication is received from the preset external device, the controller 180 can control the wireless communication unit 110 to establish the wireless communication with the preset external device. In particular, if the establishment of the wireless communication with the preset external device is available through the short range communication module 114, the controller 180 can control the short range communication module 114 to establish a short range wireless communication with the preset external device. Yet, if the wireless communication with the preset external device through the short range communication module 114 is not available, the controller 180 can establish the wireless communication with the preset external device using at least one of the mobile communication module 112 and the wireless internet module 113.

The controller 180 can control the wireless communication unit 110 to establish the wireless communication with the preset external device before a specific application (e.g., a child management application, etc.) is run. The controller 180 can control the wireless communication unit 110 to establish the wireless communication with the preset external device when a specific application (e.g., a child management application, etc.) is run. The controller 180 can control the wireless communication unit 110 to establish the wireless communication with the preset external device prior to a step S520.

The controller 180 can receive information, which is detected through a sensor of the preset external device, through the wireless communication unit 110 (S520). The information detected through the sensor of the preset external device includes at least one of third information obtained from sensing a surrounding environment of the preset external device and fourth information obtained from sensing a state of the preset user.

The controller 180 can recognize a current state of the preset user using at least one of the first information, the second information, the third information and the fourth information (S530). In particular, the controller 180 can create fifth information on a life pattern (e.g., recent sleep time, recent going-out number, etc.) of the preset user using at least one of the first information, the third information and the fourth information. And, the controller 180 can recognize a current state of the preset user using at least one of the first information, the second information, the third information, the fourth information, and the fifth information. In this instance, the current state of the preset user includes at least one of a state that a specific disease currently occurs in the preset user, a state that the preset user is doing a specific thing, and a state corresponding to an emergency.

For instance, if at least one of the third information, the fourth information and the fifth information corresponds to at least one of specific information (e.g., information on a life pattern that triggers a chest cold when the preset user gets the chest cold, information on a surrounding environment that triggers a chest cold when the preset user gets the chest cold, information on a motion of the preset user when the preset user gets the chest cold, etc.) included in the first information and specific information (e.g., information on symptoms related to a chest cold, etc.) included in the second information, the controller 180 can recognize that the current state is a state that a chest cold is currently caught.

In another instance, if specific information (e.g., information on respiration of the preset user, information on a heart rate of the preset user, etc.) included in the fourth information corresponds to information (e.g., information on respiration appearing on human sleep, information on a heart rate appearing on human sleep, etc.) on a preset sleep state previously saved in the memory 170, the controller 180 can recognize that the current state of the preset user is the sleep state.

In another instance, if specific information (e.g., information on a surrounding humidity of the preset external device, etc.) included in the third information and specific information (e.g., information on respiration of the preset user, information on a motion of the preset user, etc.) included in the fourth information correspond to information on symptoms appearing on occurrence of an emergency (e.g., a situation that a user currently sinks under the water, etc.) previously saved in the memory 170, the controller 180 can recognize that the current state of the preset user corresponds to the emergency (e.g., a situation that the preset user is currently drowning).

According to an embodiment, if the preset user's current state recognized in the step S530 using the at least one of the first information, the second information, the third information and the fourth information corresponds to a specific situation (e.g., an emergency, etc.), the controller 180 can control the output unit 150 to output preset data. In this instance, the output unit 150 includes at least one of the display unit 151, the audio output unit 152, the haptic module 153 and the optical output unit 154. Further, the preset data includes at least one of audio data, text data, optical data, video data, graphic data and vibration data.

For instance, the controller 180 can recognize that the preset user is in the water through specific information (e.g., information or a quality of surrounding air, information on surrounding humidity, etc.) included in the third information. In another instance, the controller 180 can recognize that the preset user is in a state of apnea over a preset time through specific information (e.g., information on respiration of the preset user, etc.) included in the fourth information. Using the recognized state, the controller 180 can recognize that the preset user is in the state corresponding to an emergency (e.g., a situation of sinking under the water). The controller 180 controls the output unit to output at least one of preset audio data, preset text data, preset optical data, preset video data, preset graphic data and preset vibration data, thereby enabling a user of the mobile terminal 100 to recognize that the preset user is in the emergency.

According to an embodiment, if the current state recognized in the step S530 corresponds to a preset specific situation (e.g., an emergency), the controller 180 can control the wireless communication unit 110 to transmit a specific signal to the preset external device. In particular, if a current state of a preset user corresponds to a specific situation (e.g., a situation that the preset user runs into a hoodlum, a situation that the preset user is being kidnapped, etc.), the controller 180 can control the wireless communication unit 110 to transmit a signal for ordering the preset external device to transmit audio data of recording surrounding sound of the preset external device to the preset external device.

Using the first information, the second information, the third information and the fourth information, the controller 180 can extract a cause of the recognized current state (S540). In particular, the controller 180 can create fifth information on a life pattern (e.g., recent sleep time, recent going-out number, etc.) of the preset user using at least one of the first information, the third information and the fourth information. And, the controller 180 can extract a cause of a current state of the preset user using at least one of the first information, the second information, the third information, the fourth information, and the created fifth information.

For instance, when the current state of the preset user is a chest cold caught state, if specific information (e.g., information on a recent sleep time of the preset user, etc.) included in the fifth information corresponds to specific information (e.g., information indicating that the preset user usually catches a cold if a sleep time is equal or smaller than 4 hours, etc.) included in the first information, the controller 180 can extract the specific information included in the fifth information as the cause of the current state.

In another instance, when the current state of the preset user is a chest cold caught state, if specific information (e.g., information on a temperature obtained from sensing a surrounding environment of the preset external device, etc.) included in the third information corresponds to specific information (e.g., information indicating that the preset user used to catch a cold if a measured temperature deviates from a predetermined range, etc.) included in the first information, the controller 180 can extract the specific information included in the third information as the cause of the chest cold having occurred in the preset user.

The present embodiment is advantageous because the mobile terminal 100 can check a current state of a user (or a wearer) of a preset external device. The embodiment is also advantageous in that the user of the mobile terminal 100 can obtain a cause of the current state of a preset user easily and conveniently. Meanwhile, according to an embodiment of the present invention, if a current state of a user of a preset external device is extracted, the controller 180 can control the output unit 150 to output a specific data for inducing a removal of a cause of the extracted current state of the user of the preset external device. This is described in detail with reference to FIG. 6 as follows.

Figure 6:
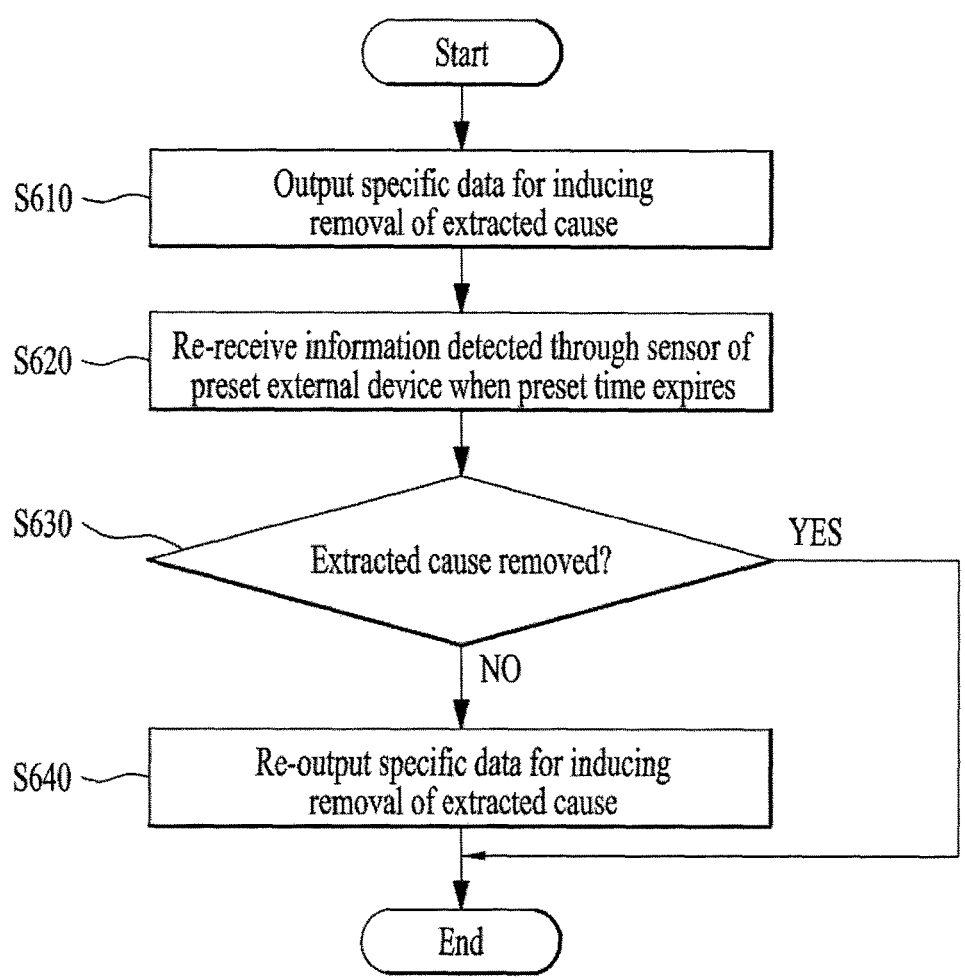
FIG. 6 is a flowchart illustrating a method of outputting specific data to induce the removal of a cause of a user's current state in a mobile terminal according to one embodiment of the present invention.

In particular, FIG. 6 is a flowchart illustrating a method of outputting specific data to induce the removal of a cause of a user's current state in a mobile terminal according to one embodiment of the present invention. Regarding FIG. 6, the contents redundant with the former description with reference to FIG. 5 are not repeated.

Referring to FIG. 6, the memory 170 can store at least one of first information on a disease history of a preset user and second information on a preset disease. The controller 180 can control the wireless communication unit 110 to receive at least one of third information obtained from sensing a surrounding environment of the preset external device and fourth information obtained from sensing a state of the preset user.

Using the first information, the second information, the third information and the fourth information, the controller 180 recognizes a current state of the preset user. The controller 180 can then extract a cause of the recognized current state of the preset user using the first information, the second information, the third information and the fourth information.

The controller 180 can control the output unit 150 to output specific data to indicate the removal of the extracted cause. In this instance, the output unit 150 includes at least one of the display unit 151, the audio output unit 152, the haptic module 153 and the optical output unit 154. And, the specific data includes at least one of audio data, text data, optical data, video data, graphic data and vibration data.

For instance, assuming that a current state of the preset user is a chest cold caught state and that a cause of the current state is extracted as excessive dust existing nearby, the controller 180 can control the display unit 151 to output a message for inducing the removal of the dust existing nearby the preset external device. In this instance, the controller 180 can control the output unit 150 to output at least one of audio data, text data, optical data, video data, graphic data and vibration data together while outputting the message. In another instance, assuming that a current state of the preset user is a chest cold caught state and that a cause of the current state is extracted as a low surrounding temperature, the controller 180 can control the display unit 151 to output a message to raise a temperature around the preset external device.

After the specific data has been output in the step S610, if a preset time expires, the controller 180 can control the wireless communication unit 110 to re-receive at least one of the third and fourth information obtained through the sensor of the preset external device (S620). In particular, after the message for inducing the removal of the extracted cause has been output, when a preset time (e.g., 1 hour) expires, the controller 180 can transmit a signal for ordering to re-obtain the third information and the fourth information to the preset external device. Subsequently, the controller 180 can control the wireless communication unit 110 to receive the re-obtained third and fourth information from the preset external device in response to the signal.

Based on at least one of the re-received third information and the re-received fourth information in the step S620, the controller 180 can determine whether or not the extracted cause is removed (S630). For instance, assuming that a current state of the preset user is a chest cold caught state and that a cause of the current state of the preset user is extracted as a low surrounding temperature, the controller 180 outputs a message for inducing a removal of the extracted cause and can then determine whether or not the extracted cause (e.g., whether the surround temperature increased) is removed based on at least one of the re-received third information and the re-received fourth information after the elapse of a predetermined time.

If the extracted cause is not removed (S630, No), the controller 180 can control the output unit 150 to re-output a specific data to induce the removal of the extracted cause. For instance, when the extracted cause is not removed based on at least one of the re-received third information and the re-received fourth information (e.g., when the surrounding temperature fails to increase), the controller 180 can control the display unit 151 to re-output the message for inducing the removal of the extracted cause.

Further, the controller 180 can control the output unit 150 to output at least one of audio data, text data, optical data, video data, graphic data and vibration data as well while outputting the message. If the controller 180 determines that the extracted cause is removed (S630, Yes), the controller 180 can display a message, which indicates that the extracted cause has been removed, to a screen of the display unit 151.

According to an embodiment, when a preset time (e.g., 1 day) expires after outputting the message indicating that the extracted cause has been removed on the display unit 151, the controller 180 can detect whether a current state of the preset user has been changed. Subsequently, the controller 180 can control a cause of the detected change of the current state of the preset user to be saved in the memory 170. For instance, if the current state of the preset user is changed into a chest cold improved state from the chest cold caught state because of the removal of the dust existing nearby, the controller 180 can control information, which indicates that the chest cold of the preset user can be improved if the dust existing nearby is removed, to be saved in the memory 170.

Moreover, the controller 180 can control information, which is created by mapping a case of excessive dust existing nearby to a case of leading the preset user to get a chest cold, to be saved in the memory 170. Thus, if a surrounding environment of the preset external device corresponds to a specific situation (e.g., a situation that excessive dust exists nearby), the controller 180 can control information, which indicates that the current state may become a specific state (e.g., a state that the preset user catches a cold), to be saved in the memory 170 by being updated continuously.

Consequently, using the recently updated information (e.g., information indicating that the preset user possibly catches a cold if excessive dust exists nearby) in the memory 170, the controller 180 can detect an existence of possibility that a current state becomes a specific state (e.g., when a preset user catches a cold) because a surrounding environment of the preset user corresponds to a specific situation (e.g., a situation that excessive dust currently exists in the surrounding environment).

If there exists the possibility the current state becomes the specific state (e.g., when the preset user catches a cold), the controller 180 outputs a specific message (e.g., a message indicating that ventilation is required since the preset user may catches a cold due to excessive dust existing nearby the preset user), thereby preventing the current state of the preset user from becoming the specific state in advance.

Meanwhile, according to an embodiment, if the controller 180 detects an existence of possibility that a current state becomes a specific state (e.g., when a preset user catches a cold), the controller 180 can recognize information, which indicates that the current state of the preset user may become the specific state at a specific timing point, using specific information (e.g., information on an incubation period of a cold, etc.) included in the second information.

Thus, the present embodiment is advantageous because a cause of a disease occurring in a user of a preset external device can become better quickly. The present embodiment is also advantageous in helping a user of the mobile terminal 100 to prevent a disease from occurring in the preset user in advance.

Figure 7:
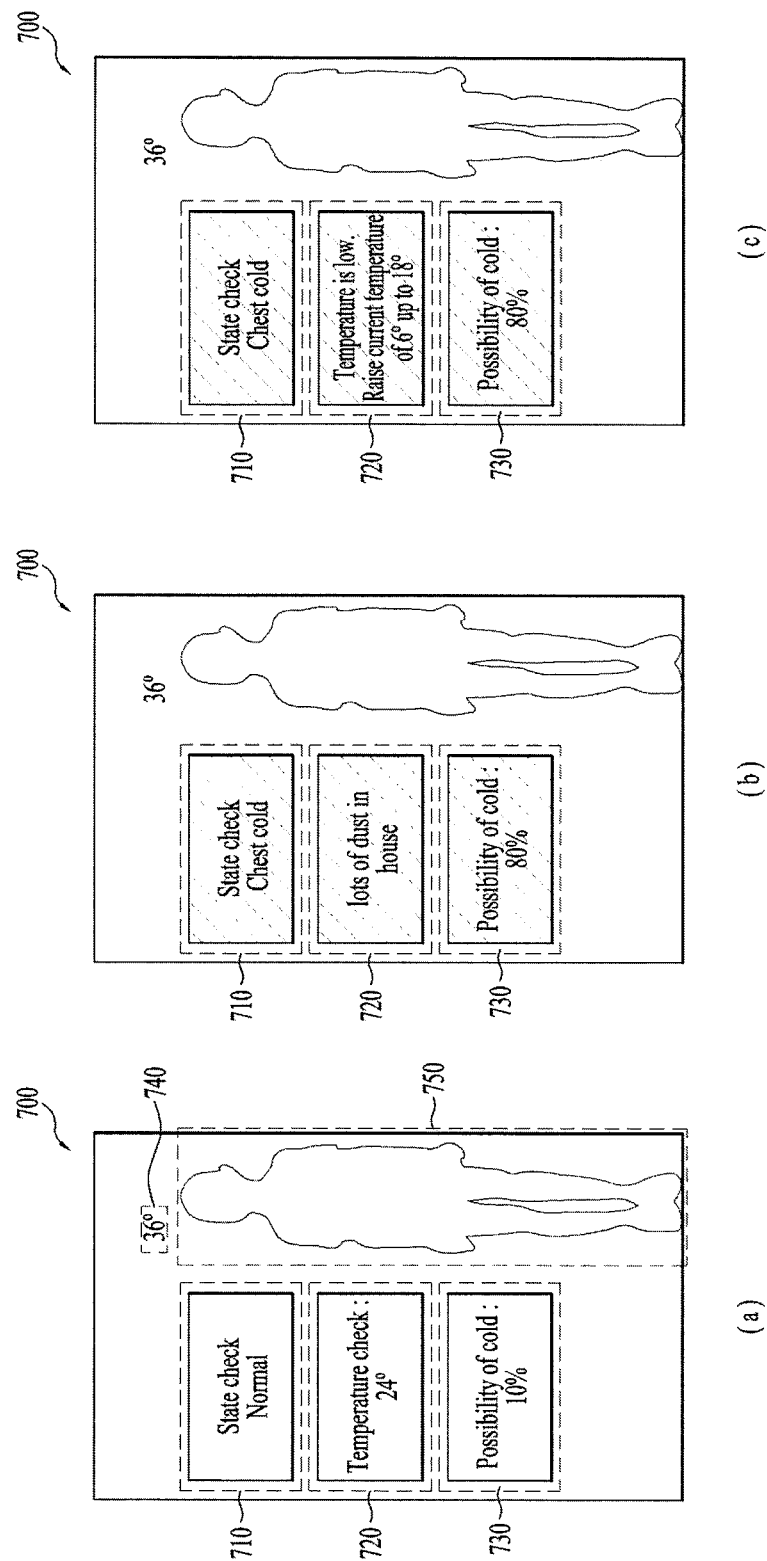
FIG. 7 is a diagram illustrating a method of providing information on a surrounding environment of a preset external device and information on a preset user in a mobile terminal according to one embodiment of the present invention.

Next, FIG. 7 is a diagram illustrating a method of providing information on a surrounding environment of a preset external device and information on a preset user in a mobile terminal according to one embodiment of the present invention. Referring to FIG. 7, if the controller 180 detects a command for executing a specific application (e.g., a child management application, etc.) previously saved in the memory 170, the controller 180 can control the display unit 151 to output an executing screen 700 of the child management application. The command for executing the child management application may be generated if a user of the mobile terminal 100 directly selects the child management application.

Alternatively, the command for executing the child management application may be generated depending on a preset condition if a signal related to the child management application is received from a preset external device. In this instance, the child management application is the application that provides at least one of information on a preset user, information on a surrounding environment of a preset external device, a current state of a preset user, and a cause of a current state of a preset user. The child management application may be saved in the memory 170 before shipment. The child management application may also be installed when upgrading an application program or firmware of the mobile terminal 100. The child management application may also be separately saved in the memory 170 by a user.

Referring to FIG. 7 (*a*), the executing screen 700 includes at least one of a first region 710 related to an output of a current state of a preset user, a second region 720 for outputting a different message depending on a cause of the current state of the preset user, a third region 730 related to an output of a value of a probability that the preset user catches a specific disease (e.g., a cold, etc.), a fourth region 740 related to an output of fourth information obtained from sensing a preset user's state received from a preset external device, and a fifth region 750 containing an image indicating the current state of the preset user.

The memory 170 can currently store first information on a disease history of a preset user and second information on a preset disease. In this instance, the first information may include information input by a user of the mobile terminal 100, information saved by being received from the preset external device periodically or aperiodically, or information received from a specific external server (e.g., a hospital server, etc.) periodically or aperiodically. The second information may include information saved in the memory 170 before shipment, information saved in the memory 170 on upgrading the child management application, information separately saved in the memory 170 by a user, or information received from a specific external server (e.g., a hospital server, etc.) periodically or aperiodically.

The controller 180 can control the wireless communication unit 110 to establish a wireless communication with a preset external device. In this instance, the wireless communication unit 110 may include at least one of the mobile communication module 112, the short range communication module 114, the wireless internet module 113, and the like. The controller 180 can receive information, which is detected through a sensor of the preset external device, through the wireless communication unit 110. The information detected through the sensor of the preset external device may include at least one of third information obtained from sensing a surrounding environment of the preset external device and fourth information obtained from sensing a state of the preset user.

The controller 180 can recognize a current state of the preset user using at least one of the first information, the second information, the third information and the fourth information. In particular, the controller 180 can create fifth information on a life pattern (e.g., recent sleep time, recent going-out number, etc.) of the preset user using at least one of the first information, the third information and the fourth information. In addition, the controller 180 can recognize a current state of the preset user using at least one of the first information, the second information, the third information, the fourth information, and the fifth information. In this instance, the current state of the preset user may include at least one of a state that a specific disease currently occurs in the preset user, a state that the preset user is doing a specific thing, and a state corresponding to an emergency.

For instance, if specific information (e.g., information on respiration of the preset user, information on a heart rate of the preset user, etc.) included in the fourth information corresponds to specific information (e.g., information on a respiration pattern on a sleep of the preset user, etc.) included in the fifth information, the controller 180 can recognize that the preset user is in a sleep state. In another instance, if specific information (e.g., a change of a location information) included in the third information and specific information (e.g., information on a motion of the preset user, information on a quantity of sweat, and information on a heart rate) included in the fourth information correspond to specific information (e.g., information required for determining whether a current state is an exercising state) previously saved in the memory, the controller 180 can recognize that a current state of the preset user is an exercising state.

In another instance, if specific information (e.g., information on a quality of air, information on a humidity, and information on an atmospheric pressure) included in the third information corresponds to specific information (e.g., information required for determining whether a current state is a swimming state) previously saved in the memory, the controller 180 can recognize that the current state of the preset user is the swimming state.

In still another instance, if specific information (e.g., information on respiration of the preset user, information on a motion of the preset user, etc.) included in the fourth information correspond to specific information (e.g., information required for determining whether a current state corresponds to an emergency) previously saved in the memory, the controller 180 can recognize that the current state of the preset user corresponds to the emergency (e.g., a situation that the preset user is kidnapped).

Meanwhile, according to an embodiment, if specific information (e.g., information on an UV value) included in the third information corresponds to specific information (e.g., information required for determining whether the preset user is located inside or outside a room) previously saved in the memory, the controller 180 cancan recognize whether the preset user is inside or outside the room.

Depending on the recognized current state of the preset user, the controller 180 can change a content of the message output to the first region 710 or may change an image included in the fifth region 750. For instance, if a value of at least one of the first information, the second information, the third information and the fourth information is included in a range of a value corresponding to a normal state previously saved in the memory, the controller 180 can display a message 'Normal state' to the first region 710 and can also output the image included in the fifth region 750 as an image indicating the normal state. Further, the controller 180 recognizes the information indicating whether the preset user is inside or outside the room and can then output the recognized information to the first region 710 together with the message on the current state of the preset user.

In another instance, if the current state of the preset user corresponds to an exercising state, the controller 180 can display a message 'Exercising' to the first region 710 and can change the image included in the fifth region 750 into an image indicating an exercising state. In particular, if the current state of the preset user corresponds to a state that the preset user is running, the controller 180 outputs a message 'Running' to the first region 710 and can change the image included in the fifth region 750 into an image indicating a running state. Moreover, if the current state of the preset user corresponds to a swimming state, the controller 180 outputs a message 'Swimming' to the first region 710 and can change the image included in the fifth region 750 into an image indicating a swimming state.

In another instance, if the current state of the preset user corresponds to a sleeping state, the controller 180 can display a message 'Sleeping' to the first region 710 and can change the image included in the fifth region 750 into an image indicating a sleeping state. In another instance, if the current state of the preset user corresponds to an emergency, the controller 180 can display a message indicating the emergency to the first region 710 and can change the image included in the fifth region 750 into an image indicating an emergency occurring state. Further, the controller 180 can change an output color of the first region 710 into a color different from an existing color. For example, if the current state of the preset user does not correspond to the emergency, the controller 180 can change the output color of the first region 710 into green. In another example, if the current state of the preset user corresponds to the emergency, the controller 180 change the output color of the first region 710 into red.

In another instance, referring to FIG. 7 (*b*) and FIG. 7 (*c*), if the current state of the preset user corresponds to a specific disease occurring state, the controller 180 outputs information on a currently occurring disease to the first region 710 and can change the image included in the fifth region 750 into an image indicating the currently occurring specific disease. For example, if the current state of the preset user corresponds to a chest cold occurring state, the controller 180 outputs a message 'Chest cold' to the first region 710 and can change the image included in the fifth region 750 into an image related to the chest cold. Further, the controller 180 can change an output color of the first region into a color different from an existing color.

Further, if there are a plurality of the recognized current states of the preset user and a plurality of the states do not conflict with one another, the controller 180 outputs a message indicating a plurality of the states of the preset user to the first region 710 and can change the image included in the fifth region into an image indicating a plurality of the states.

In particular, information on a state that a plurality of the states do not conflict with each other (i.e., a mutually non-conflicting state), information indicating what state will be displayed on the first region 710 in case of conflicting states among a plurality of the states, and information indicating what kind of image will be displayed on the fifth region 750 (by being changed from an existing image) may be previously saved in the memory 170. Using the first information, the second information, the third information and the fourth information, the controller 180 extracts a cause of the current state of the preset user. The controller 180 can then output a message, which is changed depending on the cause of the current state of the preset user, to the second region 720.

First of all, referring to FIG. 7 (*a*), if the current state of the preset user corresponds to at least one of a state of doing a specific thing and a state corresponding to an emergency, the controller 180 can display third information received from the preset external device to the second region 720. In particular, a default may be set in a manner that specific information (e.g., a surrounding temperature of a preset external device) included in the third information is output to the second region 720.

Meanwhile, if the current state of the preset user is a specific disease occurring state, the controller 180 can display one of a message indicating a cause of the current state of the preset user and a message for inducing a removal of the cause of the current state to the second region 720. For instance, referring to FIG. 7 (*b*), if the current state of the preset user corresponds to a chest cold caught state, the controller 180 can display a message (e.g., a message indicating that excessive dust exist nearby) indicating a cause of the occurrence of the chest cold to the second region 720.

In another instance, referring to FIG. 7 (*c*), if the current state of the preset user corresponds to a chest cold caught state, the controller 180 can display a message for improving the chest cold caught state to the second region 720. In particular, if the cause of the chest cold is extracted as a low temperature, the controller 180 can display a message (e.g., a message indicating that a current temperature of 6 degrees needs to be raised up to 18 degrees) for inducing the removal of the chest cold to the second region 720. Further, the message for inducing the removal of the cause of the current state may be created using specific information (e.g., information on a surrounding temperature) included in the third information and specific information (e.g., information indicating that the preset user got the chest cold if the surrounding temperature is lowered below 18 degrees) included in the first information.

Referring again to FIG. 7 (*a*), the controller 180 can display a value of probability that the preset user may catch a specific disease (e.g., a cold) to the third region 730. In this instance, the value of the probability in catching the specific disease may include a numerical value indicating an extent that a value included in at least one of the third information (e.g., information on a surrounding temperature) and the fourth information (e.g., information on a body temperature of the preset user, information on a motion of the preset user, etc.) corresponds to a value included in at least one of the first information (e.g., information indicating that the preset user caught a cold if the surrounding temperature deviates from a specific temperature, information indicating that the preset user caught a cold if a body temperature of the preset user is measured as a specific temperature, etc.) and the second information (e.g., information related to symptoms of a cold, etc.).

In the memory 170, algorithms for calculating a value of probability in catching the specific disease may be saved in advance. The controller 180 can change an output color of the third region into a color different from an existing color in accordance with a value of probability that the preset user catches a specific disease (e.g., a cold, etc.). For instance, if the probability value is smaller than a preset value (e.g., 50%), the controller 180 can change the output color of the third region into green.

Referring again to FIG. 7 (*b*) and FIG. 7 (*c*), if the probability value is equal to or greater than a preset value (e.g., 50%), the controller 180 can change the output color of the third region into red. According to an embodiment, the controller 180 can change a color of the image included in the fifth region 750 to correspond to a color of the third region 730 in accordance with the cold caught probability value.

Referring to FIG. 7 (*a*) to 7 (*c*), the controller 180 can display the fourth information to the fourth region 740. In particular, a default may be set in a manner that specific information (e.g., information on a body temperature of a preset user) included in the fourth information is output to the fourth region 740. Yet, a user can change the information output to the fourth region 740 into another specific information included in the fourth information.

The present embodiment is advantageous because a user of a mobile terminal can intuitively check various kinds of information related to a preset user through the executing screen 700. Meanwhile, if the controller 180 detects a command for selecting one of the first region 710, the second region 720 and the third region 730, the controller 180 can output information related to the selected window. This is described in detail with reference to FIGS. 8 to 11 as follows.

Figure 8:
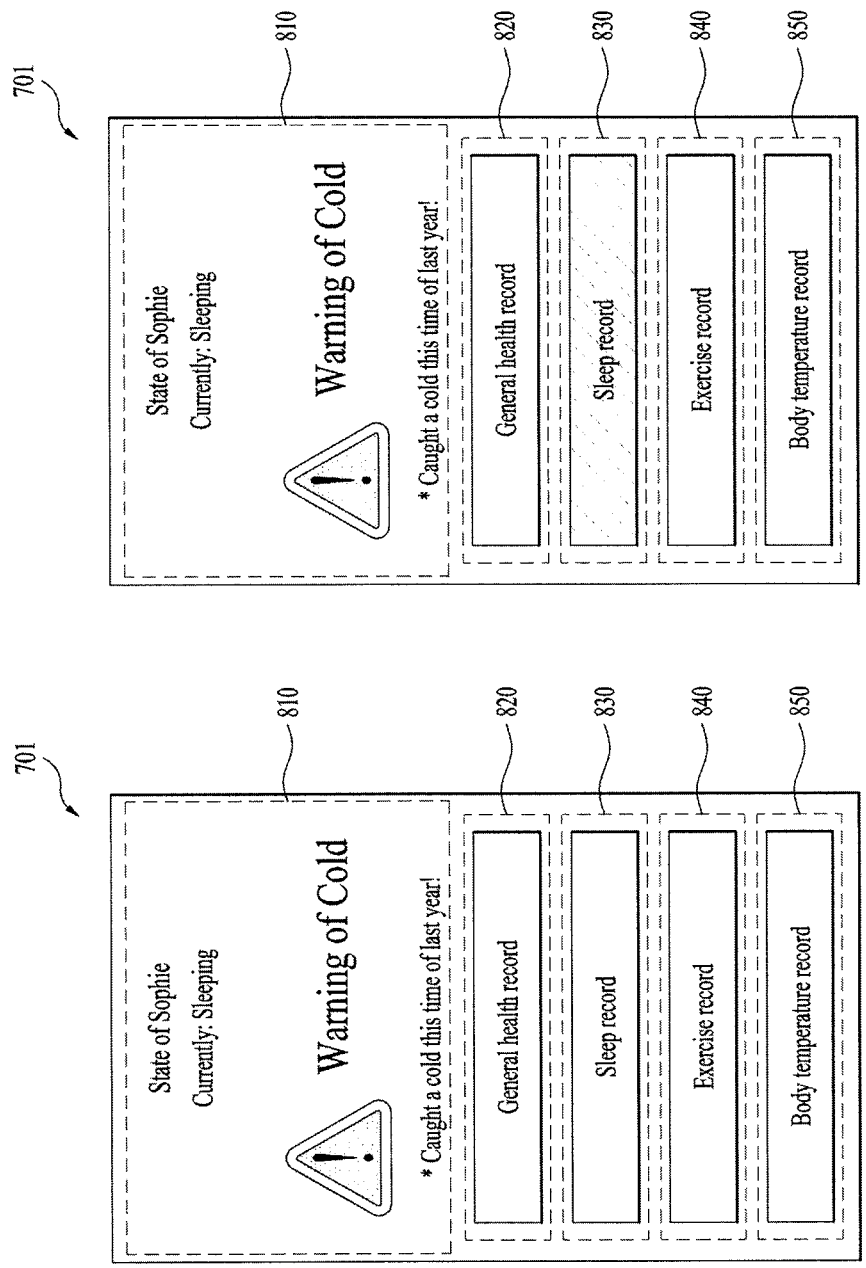
FIG. 8 is a diagram illustrating one example of a screen output in case of detecting a command for selecting a relation related to an output of a preset user's current state included in an executing screen of a child management application in a mobile terminal according to one embodiment of the present invention.

Next, FIG. 8 is a diagram illustrating one example of a screen output when detecting a command for selecting a relation related to an output of a preset user's current state included in an executing screen of a child management application in a mobile terminal according to one embodiment of the present invention. Regarding FIG. 8, the contents redundant with the former description with reference to FIG. 7 are not described.

First of all, referring to FIG. 7 (*a*), the controller 180 can detect a command for selecting a first region 710 related to an output of a current state of a preset user from a screen 700 through which a executing screen of a child management application is output. Referring to FIG. 8, if the controller 180 detects the command for selecting the first region 710, the controller 180 can display a screen 701 for outputting detailed information on a current state of a preset user. In this instance, the screen 701 includes at least one of a first region 810 for outputting detailed information on a current state of a preset user, a second region 820 related to an output of a screen for displaying a general health record of the preset user, a third region 830 related to an output of a screen indicating a sleep record of the preset user, a fourth region 840 related to a screen indicating an exercise history of the preset user, and a fifth region 850 related to an output of a screen indicating a body temperature record of the preset user.

Using at least one of first information on a disease history of the preset user saved in the memory, second information on a preset disease previously saved in the memory, third information obtained from sensing a surrounding environment, which is received from a preset external device, of the preset external device, and fourth information obtained from sensing a state of the preset user received from a preset external device, the controller 180 can recognize a current state of the preset user. Subsequently, using the first information, the second information, the third information and the fourth information, the controller 180 can extract a cause of the current state of the preset user.

The controller 180 can display detailed information on the current state of the preset user to the first region 810. In particular, the controller 180 can extract information on a disease possible to occur on a current date using specific information (e.g., information on a disease previously occurring on a date of a last year corresponding to a current date) included in the first information. For instance, if a current date is Feb. 27, 2015, the controller 180 recognizes whether there is a disease previously occurring on Feb. 27, 2015 included in the first information. If there is the disease previously occurring on Feb. 27, 2015, the controller 180 can extract information indicating that the corresponding disease may possibly occur again. Subsequently, the controller 180 creates a message using the current state of the preset user and the extracted information on the disease possible to occur on the current date and can then output the created message to the first region 810.

Referring to FIG. 8 (*b*), the controller 180 can display at least one region related to the current state among the second region 820, the third region 830, the fourth region 840 and the fifth region 850 included in the screen 701 in a color different from that of other regions. For instance, if the current state of the preset user corresponds to a sleeping state, the controller 180 can control the third region 830 related to the sleeping state to be displayed in color different from that of the first region 810, the second region 820, the fourth region 840 and the fifth region 850.

Meanwhile, if the controller 180 detects a command for selecting a prescribed one of the second region 820, the third region 830, the fourth region 840 and the fifth region 850, the controller 180 can display a screen related to the selected window. This is described in detail with reference to FIG. 9 as follows.

Figure 9:
FIG. 9 is a diagram illustrating one example of a screen output when detecting a command for selecting one of at least one or more regions included in a screen for outputting detailed information of a preset user's current state in a mobile terminal according to one embodiment of the present invention.

FIG. 9 is a diagram illustrating one example of a screen output when detecting a command for selecting one of at least one or more regions included in a screen for outputting detailed information of a preset user's current state in a mobile terminal according to one embodiment of the present invention. Regarding FIG. 9, the contents redundant with the former descriptions with reference to FIG. 7 and FIG. 8 are not described.

First of all, referring to FIG. 7 (*a*), the controller 180 can detect a command for selecting a first region 710 related to an output of a current state of a preset user from a screen 700 through which an executing screen of a child management application is output. Referring to FIG. 8, if the controller 180 detects the command for selecting the first region 710, the controller 180 can display a screen 701 for outputting detailed information on a current state of a preset user (e.g., the child). In this instance, the screen 701 includes at least one of a first region 810 displaying detailed information on a current state of the preset user, a second region 820 displaying a general health record of the preset user, a third region 830 displaying a screen indicating a sleep record of the preset user, a fourth region 840 displaying a screen indicating an exercise history of the preset user, and a fifth region 850 displaying a screen indicating a body temperature record of the preset user.

If the controller 180 detects a command for selecting one of the second region 820, the third region 830, the fourth region 840 and the fifth region 850 included in the screen 701 shown in FIG. 8 (*a*), the controller 180 can display a screen related to the selected region. In particular, using first information on a disease history of the preset user previously saved in the memory, second information on a preset disease previously saved in the memory, third information obtained from sensing a surrounding environment, which is received from a preset external device, of the preset external device, and fourth information obtained from sensing a state of the preset user received from a preset external device, the controller 180 can display the screen related to the selected region.

Referring to FIG. 9, if the controller 180 detects a command for selecting the second region 820 shown in FIG. 8 (*a*), the controller 180 can display a screen indicating a general health record using at least one of the first information, the second information, the third information and the fourth information. In this instance, the screen indicating the general health record may include at least one of information indicating whether an exercise amount of the preset user is appropriate for a preset period, information indicating whether a sleep time of the preset user is appropriate for a preset period, information indicating whether a body temperature change of the preset user is appropriate for a preset period, and a graphic data indicating a disease having occurred in a preset user for a preset period.

In this instance, the information indicating whether an exercise amount of the preset user is appropriate for a preset period, the information indicating whether a sleep time of the preset user is appropriate for a preset period, and the information indicating whether a body temperature change of the preset user is appropriate for a preset period can be displayed as specific image data. Moreover, the graphic data indicating a disease having occurred in a preset user for a preset period may include graphic data created using at least one of a disease record saved by being received from a specific external server (e.g., a hospital server, etc.) periodically or aperiodically and a disease record saved by a user's input.

Referring to FIG. 9 (*b*), if the controller 180 detects a command for selecting the third region 830 shown in FIG. 8 (*a*), the controller 180 can display a screen indicating a sleep record using at least one of the first information, the second information, the third information and the fourth information. In this instance, the screen for indicating the sleep record may include at least one of a graphic data indicating an extent of having a sound sleep of a preset user between a sleep-start hour and a sleep-end hour, a graphic data indicating information on a sound sleep time, and a text data for inducing a sound sleep of the preset user. In this instance, the text data for inducing the sound sleep may include a content provided to a user of the mobile terminal 100 to enable the preset user to have a sound sleep.

Referring to FIG. 9 (*c*), if the controller 180 detects a command for selecting the fourth region 840 shown in FIG. 8 (*a*), the controller 180 can display a screen indicating an exercise record using at least one of the first information, the second information, the third information and the fourth information. In this instance, the screen for indicating the exercise record may include at least one of a graphic data indicating an exercise amount for a preset period, a graphic data indicating information on a time for doing an exercise, and a text data containing a content for inducing the preset user to do an exercise regularly.

Referring to FIG. 9 (*d*), if the controller 180 detects a command for selecting the fifth region 850 shown in FIG. 8 (*a*), the controller 180 can display a screen indicating a body temperature record using at least one of the first information, the second information, the third information and the fourth information. In this instance, the screen for indicating the body temperature record may include at least one of a text data indicating a current body temperature of a preset user, a text data indicating a body temperature change during a preset period, a graphic data indicating a body temperature change during a preset period, and a text data for inducing a body temperature of the preset user to be maintained. In this instance, the text data for inducing the body temperature of the preset user to be maintained may include a message provided to a user of the mobile terminal 100 in order for the body temperature of the preset user not to be changed rapidly. The present embodiment is advantageous because a user of the mobile terminal 100 can intuitively recognize a change of a health state of a user of a preset external device.

Figure 10:
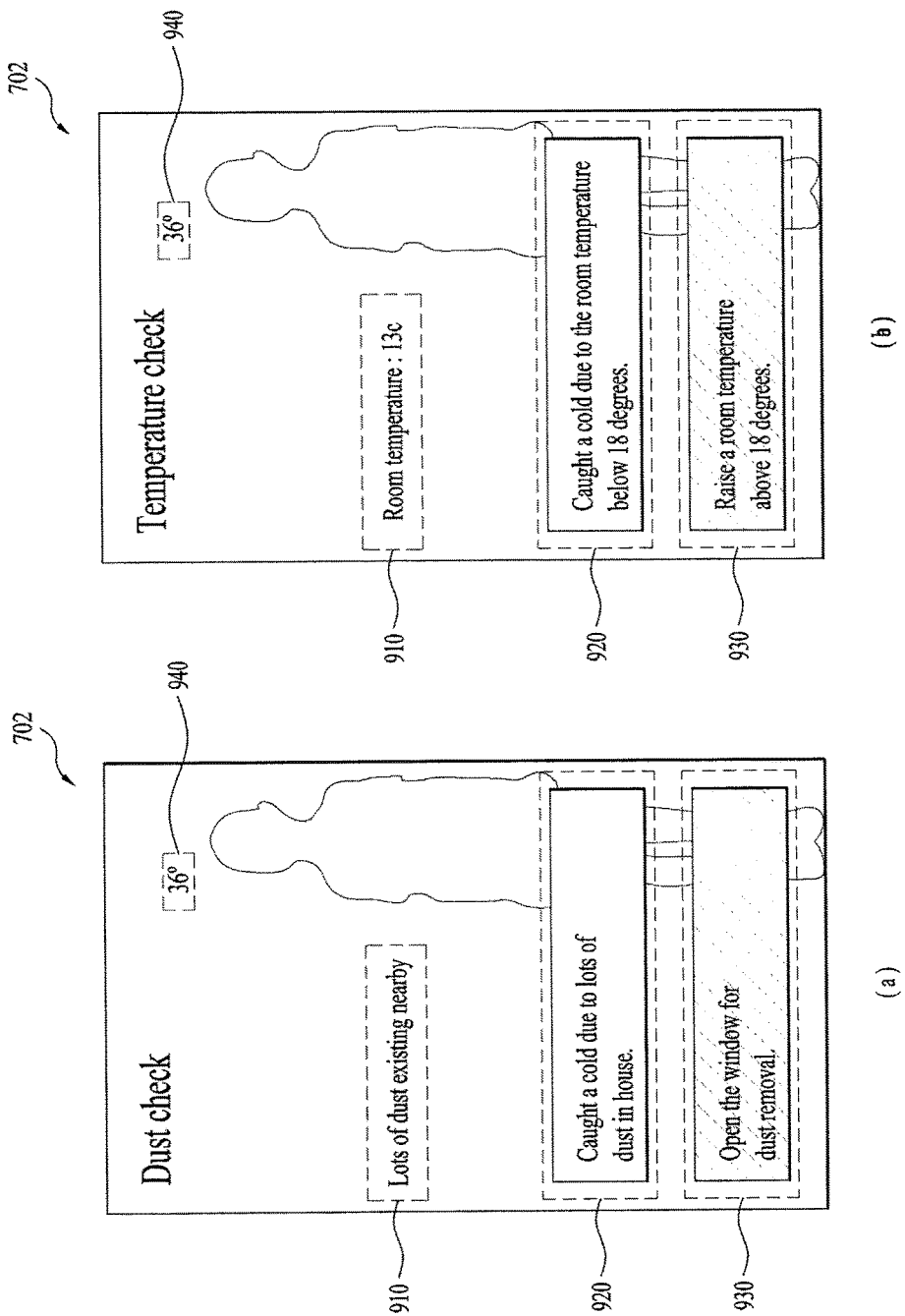
FIG. 10 is a diagram illustrating one example of a screen output when detecting a command for selecting a region for outputting a different message depending on a cause of a current state of a preset user included in an executing screen of a child management application in a mobile terminal according to one embodiment of the present invention.

FIG. 10 is a diagram illustrating one example of a screen output when detecting a command for selecting a region for outputting a different message depending on a cause of a current state of a preset user included in an executing screen of a child management application in a mobile terminal according to one embodiment of the present invention. Regarding FIG. 10, the contents redundant with the former description with reference to FIG. 7 are not described.

Referring to FIG. 10, the memory 170 can store at least one of first information on a disease history of a preset user and second information on a preset disease in advance. The controller 180 can control the wireless communication unit 110 to receive at least one of third information obtained by sensing a surrounding environment of a preset external device from the preset external device and fourth information obtained from sensing a state of the preset user.

Using the first through the fourth information, the controller 180 recognizes a current state (e.g., a cold caught state) of the preset user. The controller 180 can then extract a cause (e.g., a cause of a cold caught due to excessive dust existing nearby, a cause of a cold caught due to a surrounding temperature below a specific temperature, etc.) of the recognized current state of the preset user using the first information, the second information, the third information and the fourth information. Subsequently, referring to FIG. 7 (*b*) and FIG. 7 (*c*), the controller 180 can detect a command for selecting the second region 720 for outputting a different message in accordance with a cause of a current state of the preset user from the screen 700.

Referring to FIG. 10 (*a*) and FIG. 10 (*b*), if the controller 180 detects the command for selecting the second region 720 shown in FIG. 7 (*b*) and FIG. 7 (*c*), the controller 180 can control the display unit 151 to output a screen 702 for outputting detailed information on the cause of the current state of the preset user. The screen 702 for outputting the detailed information on the cause of the current state of the preset user may include at least one of a first region 910 for outputting the cause of the current state of the preset user, a second region 920 for outputting the detailed information on the cause of the current state of the preset user, a third region 930 for outputting a message for inducing a removal of the cause of the current state of the preset user, and a fourth region 940 for outputting specific information included in the fourth information. And, the screen 702 may include an image related to the current state of the preset user.

For instance, referring to FIG. 10 (*a*), the controller 180 can display specific information (e.g., information indicating that excessive dust exists) related to the cause of the current state included in the third information to the first region 910. The controller 180 can display detailed information (e.g., information indicating that a cold is caught due to excessive dust existing in a house) on the extracted cause of the current state to the second region 920. The controller 180 can display a message (e.g., a message indicating that a window needs to be opened to remove dust) for inducting the removal of the extracted cause of the current state to the third region 930. In addition, the controller 180 can display specific information (e.g., information on a body temperature of the preset user) included in the fourth information to the fourth region 940.

In another instance, referring to FIG. 10 (b), if the current state is a cold caught state and the cause of the current state is extracted as a surrounding temperature, the controller 180 can display specific information (e.g., information related to a surrounding temperature that is the cause of the current state) included in the third information to the first region 910. The controller 180 can display detailed information (e.g., information indicating that a cold is caught due to a temperature below a specific temperature) on the extracted cause of the current state to the second region 920. The controller 180 can display a message (e.g., a message indicating that a room temperature needs to be raised over a specific temperature) for inducting the removal of the extracted cause of the current state to the third region 930. Further, the controller 180 can display specific information (e.g., information on a body temperature of the preset user) included in the fourth information to the fourth region 940.

Figure 11:
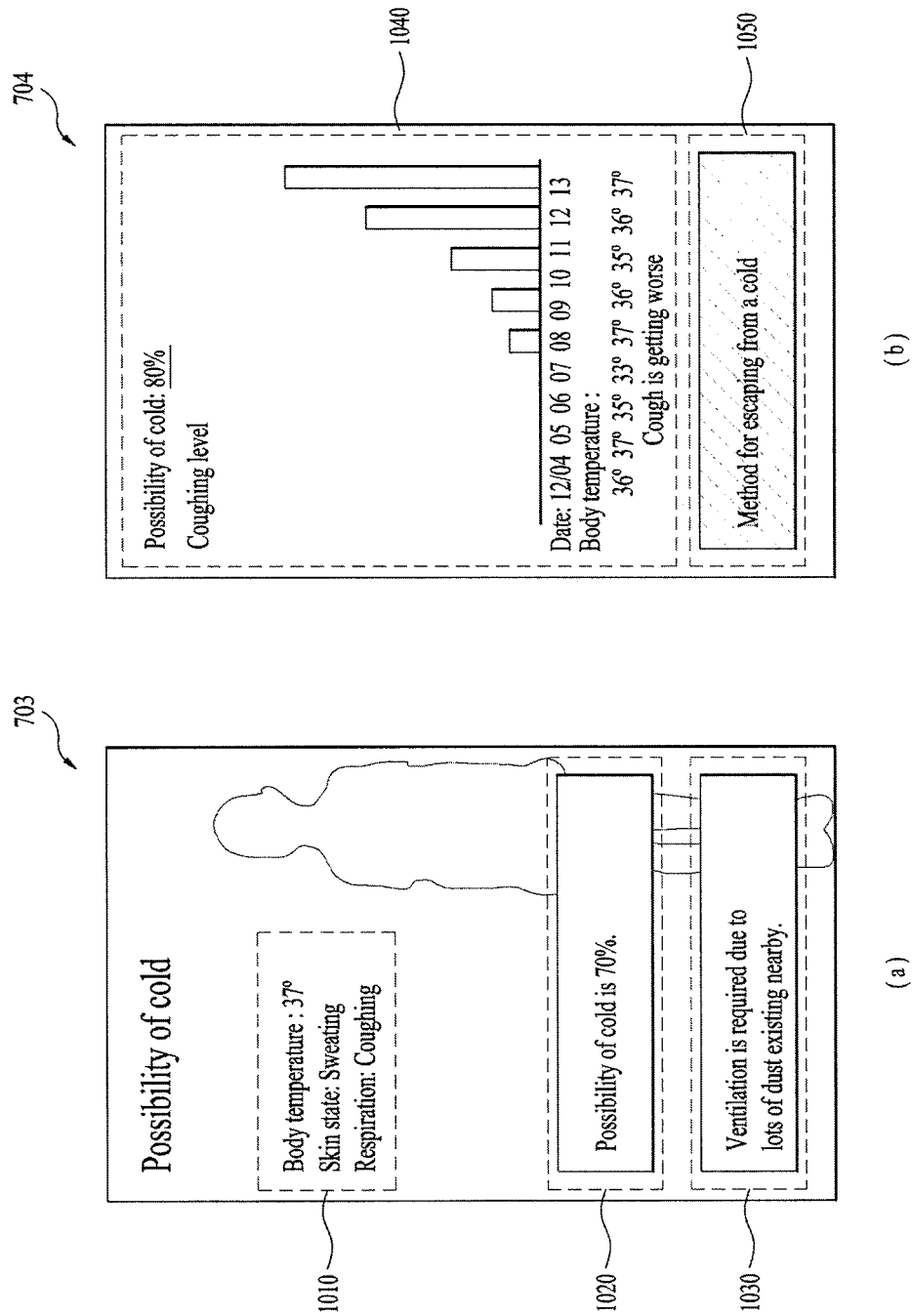
FIG. 11 is a diagram illustrating one example of a screen output when detecting a command for selecting a region related to an output of a value of probability that a present user included in an executing screen of a child management application gets a specific disease in a mobile terminal according to one embodiment of the present invention.

FIG. 11 is a diagram illustrating one example of a screen output when detecting a command for selecting a region related to an output of a value of probability that a present user included in a executing screen of a child management application will get a specific disease in a mobile terminal according to one embodiment of the present invention. Regarding FIG. 11, the contents redundant with the former description with reference to FIG. 7 are not described.

First of all, referring to FIG. 7, the controller 180 can detect a command for selecting the third region 730 for outputting a value of probability that a preset user may catch a specific disease (e.g., a cold, etc.) from the screen 700 for outputting the executing screen of the child management application. If the controller 180 detects the command for selecting the third region 730 shown in FIG. 7 (a), the controller 180 can display one of a first screen 703 shown in FIG. 11 (a) and a second screen 704 shown in FIG. 11 (b). A user can select a screen, which is to be output when the third region 730 shown in FIG. 7 (a) is selected, from the first screen 703 and the second screen 704.

Referring to FIG. 11 (a), the first screen 703 includes at least one of a first region 1010 for outputting information on the current state of the preset user, a second region 1020 for outputting a value of probability that a preset user catches a cold, and a third region 1030 for outputting a message indicating a method for lowering a value of the probability that a preset user catches a cold. In this instance, the value of the probability in catching the specific disease may include a numerical value indicating an extent that a value included in at least one of the third information (e.g., information on a surrounding temperature) and the fourth information (e.g., information on a body temperature of the preset user, information on a motion of the preset user, etc.) corresponds to a value included in at least one of the first information (e.g., information indicating that the preset user caught a cold if the surrounding temperature deviates from a specific temperature, information indicating that the preset user caught a cold if a body temperature of the preset user is measured as a specific temperature, etc.) and the second information (e.g., information related to symptoms of a cold, etc.). In the memory 170, al algorithms for calculating a value of probability in catching the cold may be saved in advance.

In the information output to the first region 1010, specific information (e.g., information on a body temperature of a preset user, information on a quantity of sweat, information indicating whether to cough, etc.) included in the fourth information may be included. The message output to the third region 1030 may include at least one of information on a nearby hospital and a method of recovering from an occurring cold.

Referring to FIG. 11 (b), the second screen 704 includes at least one of a fourth region 1040 for providing a current state of a preset user and a fifth region 1050 related to an output of information for lowering a value of probability that a preset user catches a cold. To the fourth region 1040, specific information (e.g., a change of a body temperature of the preset user during a preset period, the cold caught probability value, a graphic data indicating a cough level of the preset user, etc.) related to the current state of the preset user included in the fourth region may be output.

If the controller 180 detects a command for selecting the fifth region 1050, the controller 180 can display information, which is previously saved in the memory 170 for lowering the value of the probability that the preset user catches a cold, to the screen. Meanwhile, according to an embodiment of the present invention, if a current state of a preset user corresponds to a preset specific situation, the controller 180 can display a preset message. This is described in detail with reference to FIGS. 12 to 15 as follows.

Figure 12:
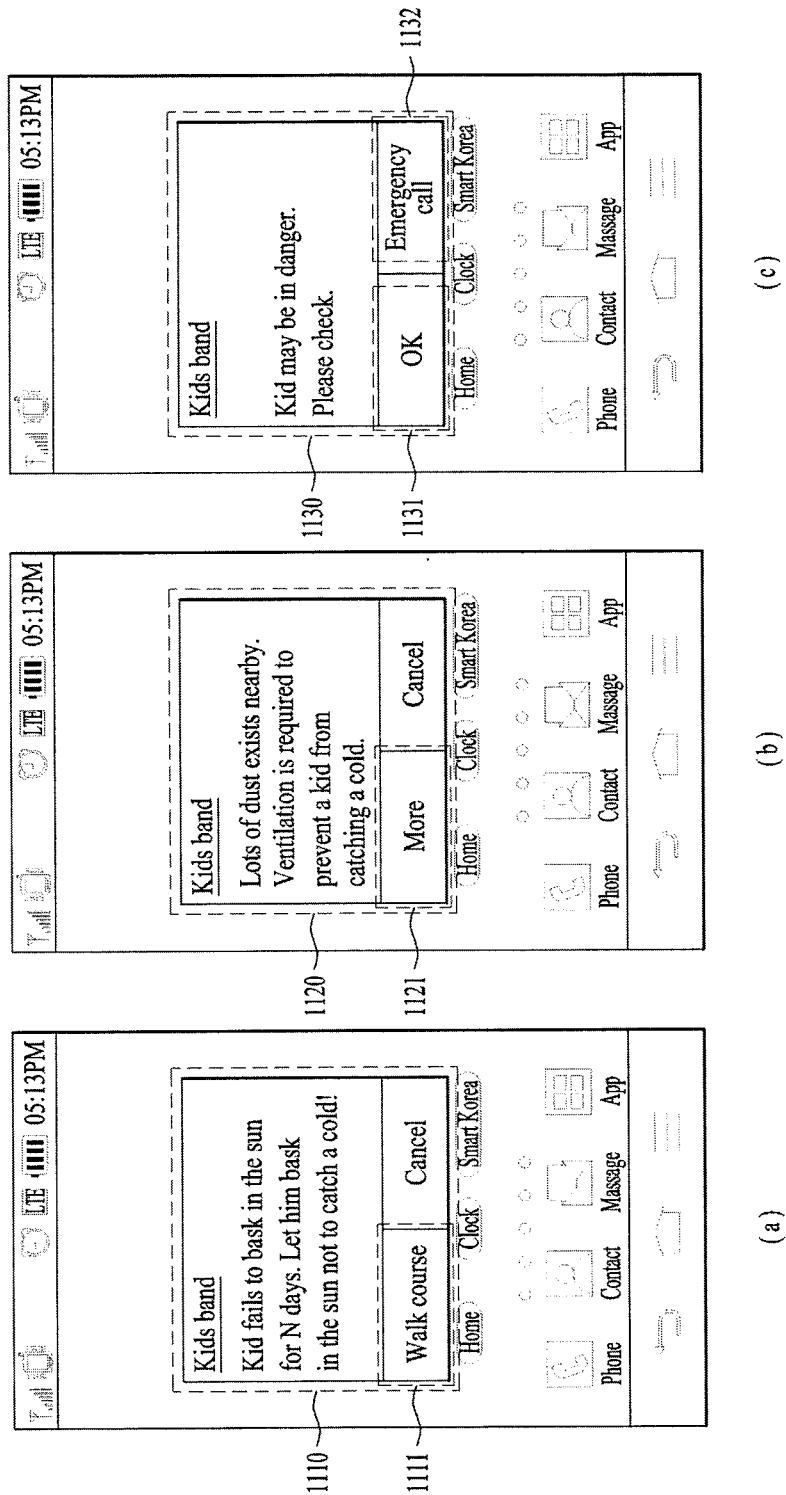
FIG. 12 is a diagram illustrating one example of a method of outputting a preset popup message if a preset user's current state corresponds to a preset specific situation in a mobile terminal according to one embodiment of the present invention.

FIG. 12 is a diagram illustrating one example of a method of outputting a preset popup message if a preset user's current state corresponds to a preset specific situation in a mobile terminal according to one embodiment of the present invention. Referring to FIG. 12, the controller 180 can run a child management application in a background. Further, the controller 180 can receive third information obtained from sensing a surrounding environment of a preset external device and fourth information obtained from sensing a state of the preset user from the preset external device connected by wireless communication. Using at least one of first information (previously saved in the memory 170) on a disease history of the preset user, second information on a preset disease previously saved in the memory, the third information and the fourth information, the controller 180 can recognize the current state of the preset user.

If the current state of the preset user corresponds to a preset specific situation, the controller 180 can display a preset message. For instance, referring to FIG. 12 (a), if the current state of the preset user corresponds to a situation of staying in a room for a preset period, the controller 180 can display a popup message 1110 for inducing the preset user to leave the room. In particular, the controller 180 recognizes a change of a UV value through the received third information, thereby being able to recognize whether the preset user has left the room for the preset period (e.g., 3 days, etc.). If the preset user fails to go out for the preset period, the controller 180 can display the popup message 1110 for inducing the preset user to go out.

The popup message 1110 includes at least one of information (e.g., information on a period for the preset user not to go out) related to the going-out of the preset user and a region 1111 related to an output of a recommended walk course. If the controller 180 detects a command for selecting the region 1111 related to the output of the recommended walk course, the controller 180 recognizes a current location information of the preset external device and can then output information on a walk course corresponding to the current location information of the preset external device. In this instance, the information on the walk course may include information previously saved in the memory 170 or information extracted through a web site search.

In another instance, referring to FIG. 12 (b), if the current state of the preset user is a state that a specific disease has occurred, the controller 180 can display a popup message 1120 for removing the current state of the preset user. For example, if the controller 180 recognizes that the preset user is in a chest cold caught state using the received third information and the received fourth information, the controller 180 can display a popup message 1120 for recovering the preset user from the specific disease occurring in the preset user.

The popup message 1120 may include the current state of the preset user, a cause of the current state of the preset user, and a content for inducing a removal of the cause of the current state. Moreover, the popup message 1120 includes a region 1121 related to an output of detailed information of the current state. If the controller 180 detects a command for selecting the region 1121 related to the output of the detailed information of the current state, the controller 180 can display the executing screen 700 of the child management application.

In another instance, referring to FIG. 12 (c), if the current state of the preset user corresponds to an emergency, the controller 180 can display a popup message 1130 indicating that an emergency has occurred in the preset user. Further, the controller 180 can control the output unit 150 to output a vibration data and audio data together with the popup message 1130. The popup message 1130 may include at least one of a message indicating that the preset user is in the emergency, a first region 1131 for checking a current situation of the preset external device, and a second region 1132 related to a function of transmitting an outgoing call signal to the preset external device.

If the controller 180 detects a command for selecting the first region 1131, the controller 180 can control the wireless communication unit 110 to transmit a specific signal (e.g., a signal for ordering to transmit audio data of recording surrounding sound of the preset external device) to the preset external device. If the controller 180 detects a command for selecting the second region 1132, the controller 180 can transmit an outgoing call signal to the preset external device. In particular, a user can make a phone call to the preset user by selecting the second region 1132.

Figure 13:
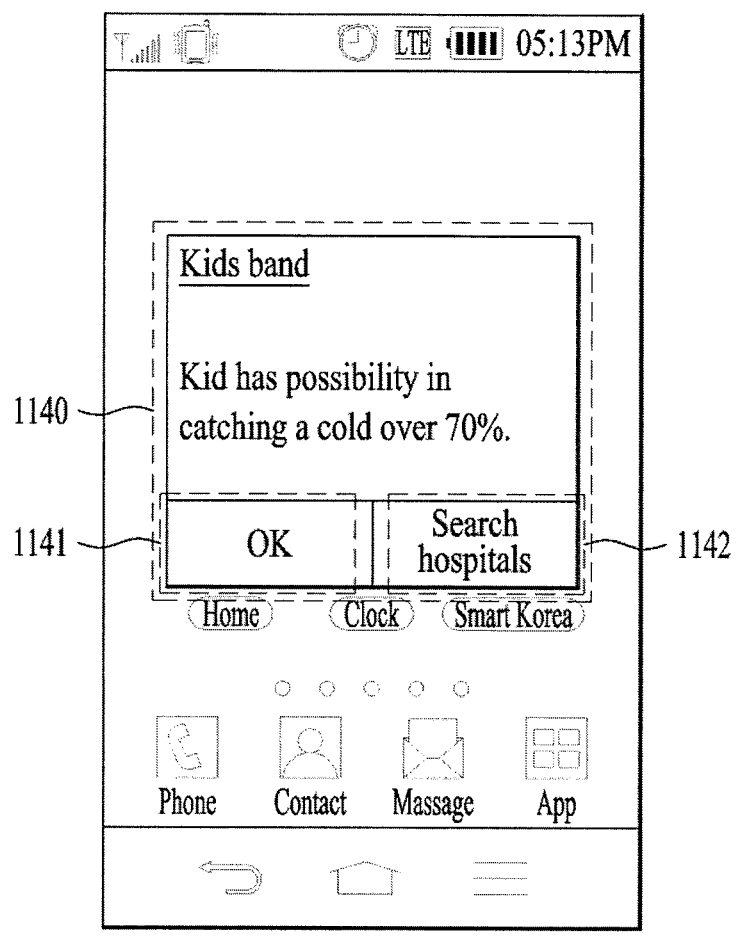
FIG. 13 is a diagram illustrating one example of a method of outputting a preset popup message if a preset user's current state corresponds to a preset specific situation in a mobile terminal according to one embodiment of the present invention.

FIG. 13 is a diagram illustrating one example of a method of outputting a preset popup message if a preset user's current state corresponds to a preset specific situation in a mobile terminal according to one embodiment of the present invention. Referring to FIG. 13, the controller 180 can run a child management application in a background. Further, the controller 180 can receive third information obtained from sensing a surrounding environment of a preset external device and fourth information obtained from sensing a state of the preset user.

Using at least one of first information (previously saved in the memory 170) on a disease history of the preset user, second information on a preset disease previously saved in the memory, the third information and the fourth information, the controller 180 can recognize the current state of the preset user. If the current state of the preset user corresponds to a preset specific situation, the controller 180 can display a preset message through the output unit 150. In this instance, the preset specific situation may include at least one of a situation that the preset user says in a room for a preset period, a situation that a specific disease has occurred in the preset user, and an emergency occurring in the preset user.

Using the first information, the second information, the third information and the fourth information, the controller 180 can recognize a value of probability that the preset user catches a specific disease. Referring to FIG. 13, if a value of probability that the preset user catches a specific disease corresponds to a preset rate (e.g., 50%), the controller 180 can display a popup message 1140 indicating that the preset user may possibly catch a cold. In this instance, the popup message 1140 may include at least one of a message indicating that the preset user may possibly catch a specific disease (e.g., a cold), a first region 1141 related to an output of detailed information of the current state, and a second region 1142 related to an output of information on a hospital corresponding to a currently located place of a preset external device.

If a command for selecting the first region 1141 is detected, the controller 180 can display the executing screen 700 of the child management application shown in FIG. 7 (a). If the controller 180 detects a command for selecting the second region 1142, the controller 180 recognizes a current location information of the preset external device and can then output information on a hospital corresponding to the current location information of the preset external device. In this instance, the information on the hospital may include information previously saved in the memory 170 or information extracted through a web site search.

According to an embodiment, if a value of probability for the preset user to catch a specific disease (e.g., a cold, etc.) corresponds to a preset rate, the controller 180 can control the output unit 150 to output at least one of audio data, text data, optical data, video data, graphic data and vibration data in accordance with the rate value together with the popup message 1140. For example, if the value of the probability for the preset user to catch the cold is equal to or greater than 20% but smaller than 40%, the controller 180 can display the popup message 1140. In another example, if the value of the probability for the preset user to catch the cold is equal to or greater than 40% but smaller than 80%, the controller 180 can control the output unit 150 to output a vibration data together with the popup message 1140. For further example, if the value of the probability for the preset user to catch the cold is equal to or greater than 80% but equal to or smaller than 100%, the controller 180 can control the output unit 150 to output a vibration data and audio data together with the popup message 1140.

In some cases, if a value of probability that the preset user catches a specific disease corresponds to a preset rate, the controller 180 can display the popup message 1140, which indicates that the preset user may possibly catch a cold, plural times. Meanwhile, according to an embodiment of the present invention, if the controller 180 recognizes that the current state of the preset user is a sleeping state, the controller 180 can transmit a specific signal for setting an alarm at a preset external device to the preset external device. This is described in detail with reference to FIG. 14 as follows.

Figure 14:
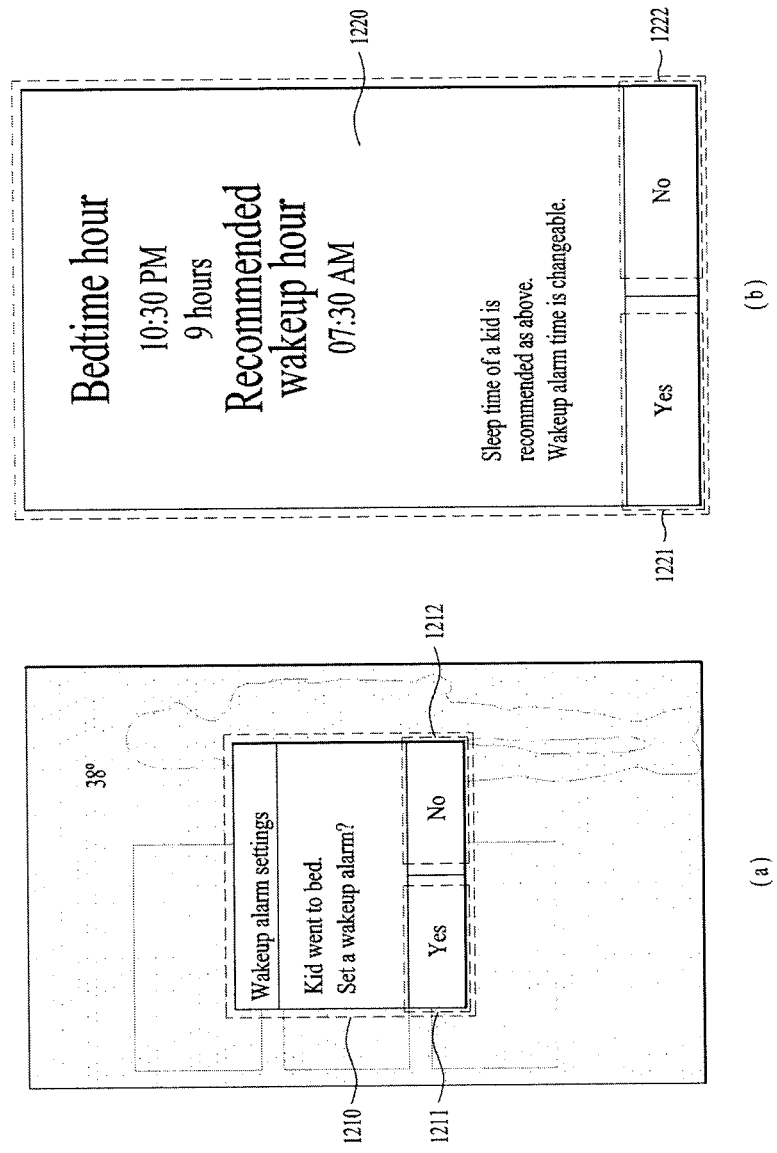
FIG. 14 is a diagram illustrating one example of a method of outputting a preset popup message if a preset user's current state corresponds to a preset specific situation in a mobile terminal according to one embodiment of the present invention.

FIG. 14 is a diagram illustrating one example of a method of outputting a preset popup message if a preset user's current state corresponds to a preset specific situation in a mobile terminal according to one embodiment of the present invention. First of all, referring to FIG. 7, if the controller 180 detects a command for executing a child management application previously saved in the memory 170, the controller 180 can control the display unit 151 to output the executing screen 700 of the child management application.

Using at least one of first information (previously saved in the memory 170) on a disease history of the preset user, second information on a preset disease previously saved in the memory, third information obtained by sensing a surrounding environment of the preset external device received from the preset external device, and fourth information obtained from sensing the state of the preset user received from the preset external device, the controller 180 can recognize the current state of the preset user.

If the current state of the preset user corresponds to a preset specific situation, the controller 180 can display a preset message. For instance, referring to FIG. 14 (a), if the current state of the preset user corresponds to a sleeping state, the controller 180 can display a message 1210 for checking whether to set an alarm at the preset external device.

Referring to FIG. 14 (b), if the controller 180 detects a command for selecting the first region 1211 related to the command for setting the alarm included in the message 1210, the controller 180 can display a screen 1220 for setting an alarm in the preset external device. In the screen 1220, at least one of information on a recommended sleep time previously saved in the memory 170 and information on an alarm time to be set based on the information on the recommended sleep time can be included.

If the controller 180 detects a command for selecting a third region 1221 related to the command for setting the alarm through the screen 1220 for setting the alarm in the preset external device, the controller 180 can transmit a signal for setting the alarm in the preset external device to the preset external device. Meanwhile, if the controller 180 detects a command for selecting a second region 1212 shown in FIG. 14 (a) or a command for selecting a fourth region 1222 shown in FIG. 14 (b), the controller 180 can not transmit the signal for setting the alarm in the preset external device. The present embodiment is advantageous in helping a preset user to have a regular sleep habit.

Figure 15:
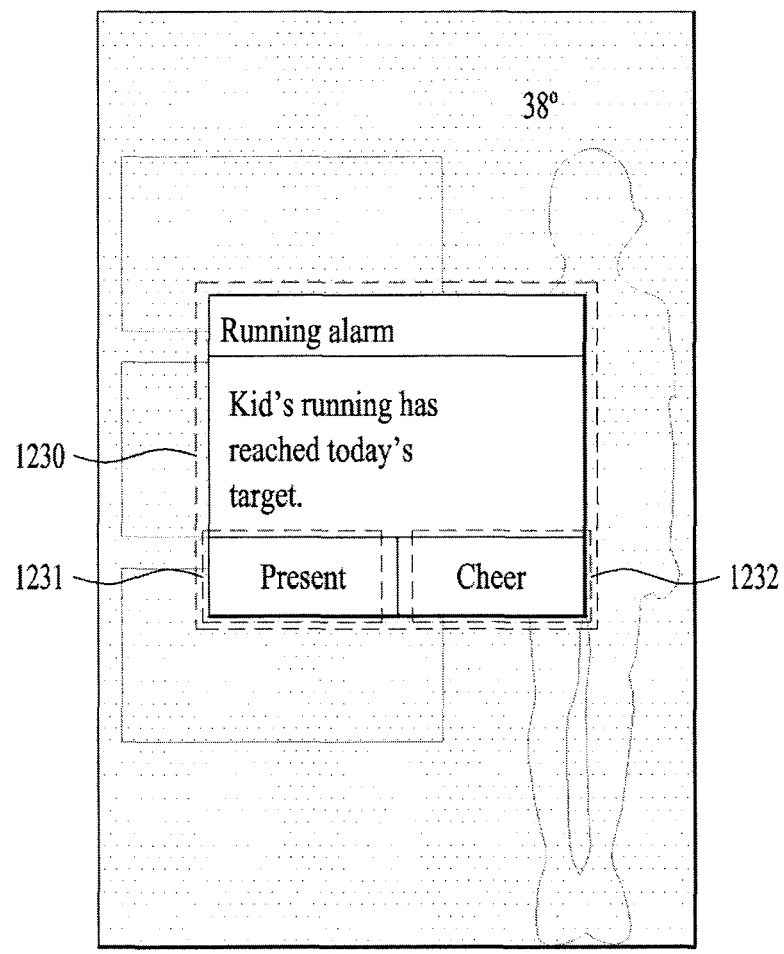
FIG. 15 is a diagram illustrating one example of a method of outputting a preset popup message if a preset user's current state corresponds to a preset specific situation in a mobile terminal according to one embodiment of the present invention.

FIG. 15 is a diagram illustrating one example of a method of outputting a preset popup message if a preset user's current state corresponds to a preset specific situation in a mobile terminal according to one embodiment of the present invention. First of all, referring to FIG. 7, if the controller 180 detects a command for executing a child management application previously saved in the memory 170, the controller 180 can control the display unit 151 to output the executing screen 700 of the child management application.

Using at least one of first information on a disease history of the preset user previously saved in the memory, second information on a preset disease previously saved in the memory, third information obtained from sensing a surrounding environment, which is received from a preset external device, of the preset external device, and fourth information obtained from sensing a state of the preset user received from a preset external device, the controller 180 can recognize a current state of the preset user. If the preset user corresponds to a preset specific situation, the controller 180 can display a preset message.

Referring to FIG. 15, if a state of the preset user corresponds to a situation that an exercise target is achieved, the controller 180 can display a message 1230 indicating that the preset user has achieved the exercise target. As shown, the message 1230 includes at least one of a first region 1231 related to a function of transmitting a specific signal (e.g., a signal for sending a present to the preset user, etc.) to the preset external device and a second region 1232 related to a function of sending a specific message (e.g., a message for cheering the preset user, etc.) to the preset external device. If the controller 180 detects a command for selecting one of the first region 1231 and the second region 1232 included in the message 1230, the controller 180 can transmit at least one of the specific signal and the specific message to the preset external device.

In the following descriptions with reference to FIGS. 16 to 24, a case that the external device described with reference to FIGS. 5 to 15 is a mobile is taken as an example. In particular, the mobile terminal may include the mobile terminal 300 of the watch type described with reference to FIG. 3 or a mobile terminal of a band type. In the following description, assume a case that an external device includes the mobile terminal 300 of the watch type or the mobile terminal of the band type. For clarity of the following description, the external device is named a mobile terminal 1400 to distinguish the mobile terminal 300 of the watch type and the mobile terminal of the band type from each other. When an external device is the mobile terminal 300 of the watch type or the mobile terminal of the band type, the description of the components (reference numbers included) shown in FIG. 1A can be referred to. However, the mobile terminal 1400 of embodiments described with reference to FIGS. 16 to 24 is non-limited by the mobile terminal 300 of the watch type shown in FIG. 3 or the mobile terminal of the band type and may further include one of a glass type terminal (e.g., a smart glass), an HMD (head mounted display), a headset and the like.

Figure 16:
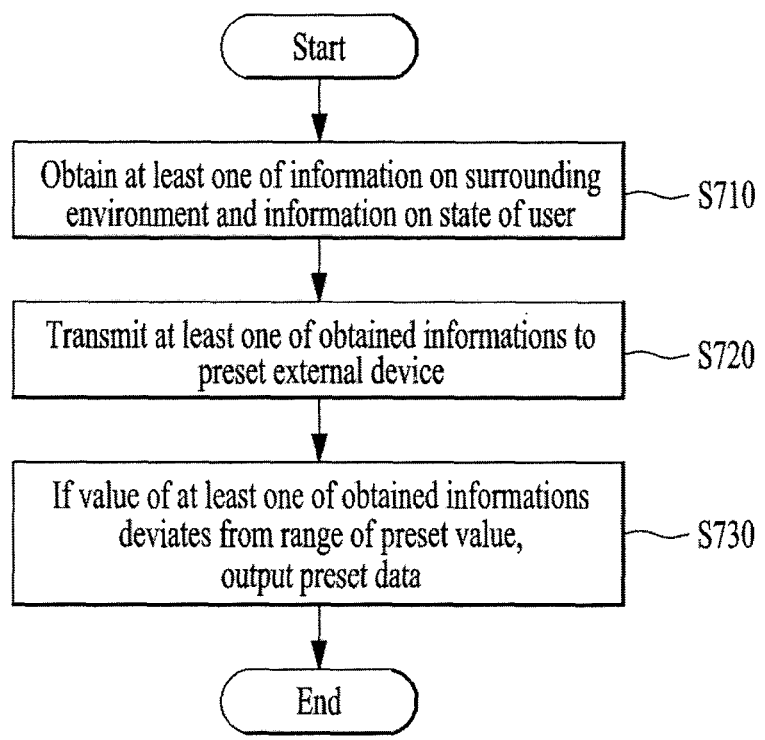
FIG. 16 is a flowchart illustrating one example of a method of sending information on a surrounding environment and information on a user's state to a preset external device and outputting preset data in a mobile terminal of a watch type according to one embodiment of the present invention.

A method of transmitting various kinds of information obtained through sensors to a preset external device and outputting preset data in a mobile terminal 1400 according to one embodiment of the present invention is described in detail with reference to FIGS. 16 to 24 as follows. In particular, FIG. 16 is a flowchart illustrating one example of a method of sending information on a surrounding environment and information on a user's state to a preset external device and outputting preset data in a mobile terminal of a watch type according to one embodiment of the present invention. Referring to FIG. 16, the controller 180 of the mobile terminal 1400 can control the wireless communication unit 110 to establish a wireless communication with a preset external device. In this instance, the wireless communication unit 110 may include at least one of the mobile communication module 112, the short range communication module 114, and the wireless internet module 113.

The controller 180 can control the sensing unit 140 to obtain at least one of first information on a surrounding environment and second information on a state of a user (S710). In this instance, the first information is the information obtained from sensing a surrounding environment periodically or aperiodically through a sensor and may include at least one of information on an amount of nearby dust, information on a current location, information on a quality of air, information on a surrounding temperature, information on a surrounding atmospheric pressure, and information on a surrounding humidity. The second information is the information obtained from sensing a state of the preset user periodically or aperiodically through a sensor and may include at least one of information on respiration of a user, information on a quantity of sweat of a user, information on a motion of a user, information on a heart rate of a user, information on a body temperature of a user, and information on a skin temperature of a user.

The sensing unit 140 may include at least one of a proximity sensor 141, an illumination sensor 142, a touch sensor, an acceleration sensor, a magnetic sensor, a G-sensor, a gyroscope sensor, a motion sensor, an RGB sensor, an IR (infrared) sensor, a finger scan sensor, an ultrasonic sensor, an optical sensor (e.g., the camera 121), a microphone 122, a battery gauge, an environment sensor (e.g., a barometer, a hygrometer, a radioactivity detection sensor, a heat detection sensor, a gas detection sensor, etc.), a chemical sensor (e.g., an electronic nose, a health care sensor, a biometric recognition sensor, etc.), a GSR (Galvanic Skin Response) sensor, a PPG (Photoploethysmogram) sensor, a UV (Ultraviolet-ray) sensor, a skin temperature detection sensor, a gas sensor, a band circumference length measurement sensor, and the like.

The controller 180 can transmit at least one of the first information and the second information to the preset external device (S720). According to an embodiment, if a value of at least one of the first information and the second information obtained in the step S710 deviates from a range of a preset first value, the controller 180 can control the output unit 150 to output a preset first data (S730). In this instance, the output unit 150 may include at least one of the display unit 151, the audio output unit 152, the haptic module 153 and the optical output unit 154. In addition, the first data may include at least one of audio data, text data, optical data, video data, graphic data and vibration data.

For instance, if a temperature of the surrounding environment in the first information obtained in the step S710 deviates from the range of a preset first value (e.g., a range of a value corresponding to a temperature for a user not to catch a cold), the controller 180 can control the output unit 150 to output a message indicating the change of the surrounding temperature together with at least one of audio data, optical data and vibration data. Further, after the message has been output, until the user checks the contents of the message, the controller 180 can display the message together with at least one of the audio data, the optical data and the vibration data.

According to an embodiment, if the controller 180 receives a specific signal from the preset external device, the controller 180 can display a preset second data different from the first data through the output unit 150. For instance, if the controller 180 receives a signal for requesting a confirmation of a current state of a user from the preset external device, the controller 180 can control the output unit to output a preset second data (e.g., a text data indicating that a confirmation of a current state is requested) different from the first data.

Meanwhile, according to an embodiment, if a value of at least one of the first information and the second information corresponds to a range of a preset second value, the controller 180 controls the wireless communication unit 110 to transmit a specific signal to a preset external device and can also control the output unit 150 to output a preset third data different from each of the first data and the second data. This shall be further described in detail with reference to FIGS. 21 to 24 later.

According to an embodiment, if a value of at least one of the first information and the second information corresponds to a range of a preset second value, the controller 180 can control the wireless communication unit 110 to transmit a specific signal to a plurality of preset external devices. For instance, if a value of at least one of the first information and the second information corresponds to a range of a value corresponding to an emergency (e.g., a situation of sinking under the water), the controller 180 can control the wireless communication unit 110 to transmit a signal including a message indicating the emergency to a plurality of preset external devices.

According to an embodiment, after the first data has been output through the output unit 150 in the step S730, if a preset time expires, the controller 180 controls the sensing unit 140 to re-obtain at least one of the first information and the second information. If a value of at least one of the re-obtained first information and the re-obtained second information deviates from the range of the preset first value, the controller 180 can control the first data to be re-output through the output unit 150. For instance, after the first data has been output in the step S730, if the preset time (e.g., 10 minutes) expires, the controller 180 can control the sensing unit 140 to re-obtain specific information (e.g., a temperature of a surrounding environment, etc.) included in the first information having deviated from the range of the preset first value. If the re-obtained specific information (e.g., the temperature of the surrounding environment, etc.) in the first information deviates from the rage of the preset first value (e.g., a range of a value corresponding to a temperature for a user not to catch a cold), the controller 180 can control the output unit 150 to re-output the first data.

According to an embodiment, the controller 180 recognizes a time for a battery to supply a power. If the recognized time is equal to or smaller than a preset time (e.g., 30 minutes), the controller 180 can transmit a specific signal, which includes a message indicating that a battery of the mobile terminal 100 needs to be charged, to an external device. Meanwhile, according to an embodiment, the mobile terminal 1400 includes a band wearable on a user body and at least one portion of the output unit 150 may configure at least one portion of the band 302. This is further described in detail with reference to FIG. 17 as follows.

Figure 17:
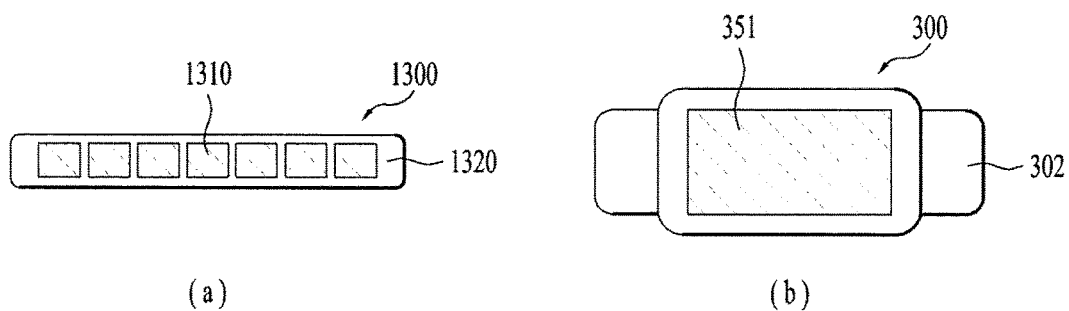
FIG. 17 is a diagram illustrating one example that at least one portion of an output unit configures at least one portion of a band in a mobile terminal according to one embodiment of the present invention.

FIG. 17 is a diagram illustrating one example that at least one portion of an output unit configures at least one portion of a band in a mobile terminal according to one embodiment of the present invention. Referring to FIG. 17, at least one portion of the output unit 150 of the mobile terminal 1400 may configure at least one portion of a band. In this instance, the output unit 150 includes at least one of the display unit 151, the audio output unit 152, the haptic module 153 and the optical output unit 154. And, the band may be formed of a flexible material and a length of the band may be adjustable.

For instance, referring to FIG. 17 (a), a mobile terminal 1300 of a band type includes a band 1320 having at least one of at least one optical output unit 1310, an audio output unit and a haptic module. In another instance, referring to FIG. 17 (b), a mobile terminal 300 of a watch type includes at least one of a band 1320, a display unit 351, an audio output unit (not shown in the drawing), a haptic module, and an optical output unit.

Meanwhile, according to an embodiment of the present invention, since a band of the mobile terminal 1400 is length-adjustable, a part on which the mobile terminal 1400 is wearable is non-limited by a specific part. And, the mobile terminal 1400 is wearable on a part (e.g., a wrist, a forearm, a hill, a calf, etc.) of a user body desired by a user. However, information obtained through a sensor may be changeable depending on the part having the mobile terminal 1440 worn thereon. Hence, the controller 180 should obtain information on a location at which the mobile terminal 1400 is worn. This is further described in detail with reference to FIG. 18 as follows.

Figure 18:
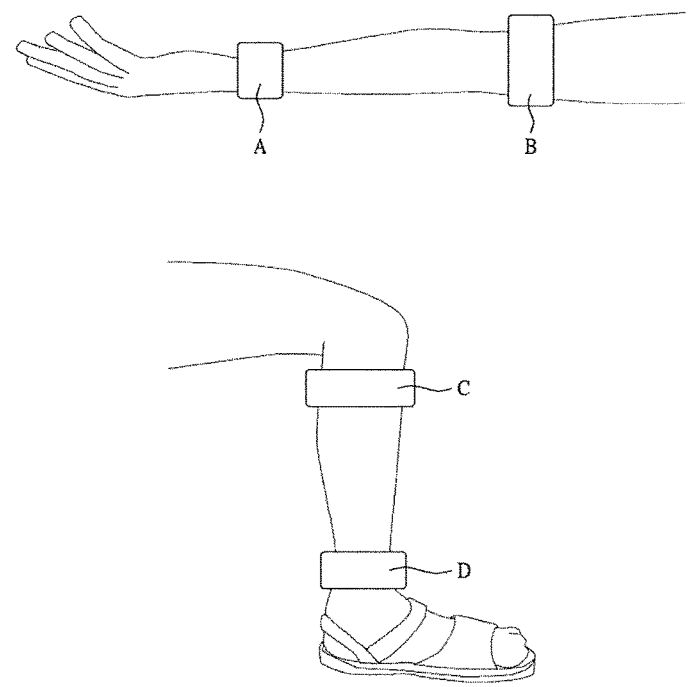
FIG. 18 is a diagram illustrating one example of a method of obtaining information on a mobile terminal worn location in a mobile terminal according to one embodiment of the present invention.

FIG. 18 is a diagram illustrating one example of a method of obtaining information on a mobile terminal worn location in a mobile terminal according to one embodiment of the present invention. Referring to FIG. 18, the mobile terminal 1400 can be worn on one of a first region A corresponding to an elbow of a user body, a second region B corresponding to a forearm of the user body, a third region C corresponding to a calf of the user body, and a fourth region D corresponding to an ankle of the user body. Yet, the worn location of the mobile terminal 1400 is non-limited by the above-listed regions. And, the mobile terminal 1400 can be worn on other regions of the user body as well as on the above-listed regions.

The controller 180 can obtain at least one of information on a heart rate of a user and information on a circumferential length of a band using a specific sensor (e.g., a PPG sensor, a band circumference length measurement sensor, etc.) included in the sensing unit 140. If at least one of the obtained information on the heart rate of the user and the information on the circumferential length of the band corresponds to information on a circumferential length of the band in case of wearing the mobile terminal 1400 on a specific region (e.g., the first region A) and information on a heart rate in case of wearing the mobile terminal 1400 on a specific region (e.g., the first region A), the controller 180 can recognize a worn location of the mobile terminal as the specific region (e.g., the first region A).

An algorithm for recognizing a worn location of a mobile terminal may be previously saved in the memory 170 of the mobile terminal 1400. At least one of information on a worn location of a mobile terminal corresponding to a circumferential length of a band and information on a worn location of a mobile terminal corresponding to a heart rate may be previously saved in the memory 170 of the mobile terminal 1400.

According to the present embodiment, the controller 180 recognizes information on a worn location of the mobile terminal 1400 and can then obtain more accurate information using the recognized information in compensating for information to be obtained through a sensor. Meanwhile, according to an embodiment of the present invention, it can output a data differing in accordance with a value of at least one of first information on a surrounding environment and second information on a state of a user. This is described in detail with reference to FIGS. 19 to 24 as follows.

Figure 19:
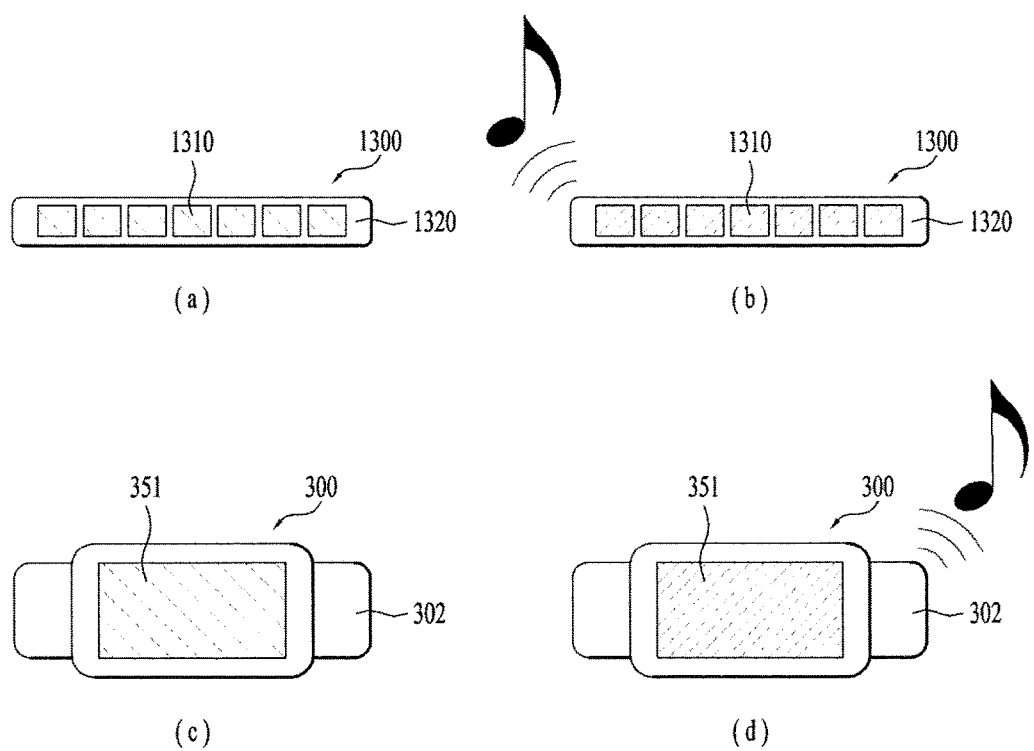
FIG. 19 is a diagram illustrating one example of a method of outputting a different data depending on a value of at least one of information on a surrounding environment and information on a user's state in a mobile terminal according to one embodiment of the present invention.

FIG. 19 is a diagram illustrating one example of a method of outputting a different data depending on a value of at least one of information on a surrounding environment and information on a user's state in a mobile terminal according to one embodiment of the present invention. Referring to FIG. 19, the controller 180 of the mobile terminal 1400 can control the sensing unit 140 to obtain at least one of first information on a surrounding environment and second information on a state of a user. If a value of at least one of the first information and the second information deviates from a range of a preset first value, the controller 180 can display a preset first data through the output unit 150. In this instance, the output unit 150 may include at least one of a display unit, an audio output unit, a haptic module and an optical output unit. Further, the first data may include at least one of audio data, text data, optical data, video data, graphic data and vibration data.

If a value of at least one of the first information and the second information is included in a range of a preset second value, the controller 180 can control the output unit to output second data different from the first data. In this instance, the second data may include at least one of audio data, text data, optical data, video data, graphic data and vibration data.

In particular, if types of current states of a user are different from each other, the controller 180 of the mobile terminal 1400 can control the output unit to output different data. For instance, if a value of at least one of the first information and the second information deviates from a range of a value for a user not to catch a cold, the controller 180 can control the output unit 150 to output a preset first data. In another instance, if a value of at least one of the first information and the second information is included in a range of a second value corresponding to an emergency of a user, the controller 180 can display a preset second data different from the first data.

Referring to FIG. 19 (*a*) and FIG. 19 (*b*), a mobile terminal 1300 of a band type includes a band 1320 having at least one of at least one optical output unit 1310, an audio output unit (not shown in the drawing), a haptic module (not shown in the drawing), and a sensing unit (not shown in the drawing). For clarity of the following description, assume that the mobile terminal 1400 shown in FIG. 19 (*a*) and FIG. 19 (*b*) is the mobile terminal 1300 of the band type, by which the present embodiment is non-limited. For instance, the mobile terminal 1400 may include the mobile terminal 300 of the watch type.

Referring to FIG. 19 (*a*), if specific information (e.g., information on a surrounding temperature, etc.) included in the first information deviates from a range (e.g., a range of a temperature value for a user not to catch a cold, etc.) of a preset first value, the controller 180 of the mobile terminal 1300 of the band type can control the optical unit 1310 to output first data (e.g., an optical data of outputting blue).

Referring to FIG. 19 (*b*), if a value of at least one of specific information (e.g., information on a surrounding humidity, etc.) included in the first information and specific information (e.g., information on respiration of a user, information on a motion of a user, etc.) included in the second information is included in a range (e.g., a range of a value corresponding to an emergency that a user is sinking under the water) of a preset second value, the controller 180 of the mobile terminal 1300 of the band type can control the output unit 150 to output second data (e.g., optical data of outputting a color different from that of the first data and audio data) different from the first data.

According to an embodiment, if a value of at least one of the first information and the second information corresponds to a range (e.g., a range of a value corresponding to an emergency that a user is sinking under the water) of a preset second value, the controller 180 can control the wireless communication unit 110 to transmit a specific signal to a preset external device. In some cases, the controller 180 can control the wireless communication unit 110 to transmit the specific signal to a plurality of preset external devices.

Meanwhile, although types of current states of a user are identical to each other, the controller 180 of the mobile terminal 1400 may control the output unit to output different data depending on an extent of the current state. For instance, if a value of at least one of the first information and the second information is included in a range of a value corresponding to a case that a user has a mild fever, the controller 180 of the mobile terminal 1400 can control the output unit 150 to output second data. In another instance, if a value of at least one of the first information and the second information is included in a range of a value corresponding to a case that a user has a high fever, the controller 180 of the mobile terminal 1400 can control the output unit to output third data different from the second data.

Referring to FIG. 19 (*c*) and FIG. 19 (*d*), a mobile terminal 300 of a watch type includes a band 302, a display unit 351, an audio output unit (not shown in the drawing), a haptic module (not shown in the drawing), an optical output unit (not shown in the drawing), and a sensing unit (not shown in the drawing). For clarity of the following description, assume that the mobile terminal 1400 shown in FIG. 19 (*c*) and FIG. 19 (*d*) is the mobile terminal 300 of the watch type, by which the present embodiment is non-limited. For instance, the mobile terminal 1400 may include the mobile terminal 1300 of the band type.

Referring to FIG. 19 (c), if specific information (e.g., information on a body temperature of a user) included in the second information is included in a range (e.g., a range of a value corresponding to a case that a user has a mild fever) of a preset third value, the controller 180 of the mobile terminal 300 can control the display unit 351 to output third data (e.g., a text data indicating that a user is currently in a state of having a mild fever).

Referring to FIG. 19 (d), if specific information (e.g., information on a body temperature of a user) included in the second information is included in a range (e.g., a range of a value corresponding to a case that a user has a high fever) of a preset fourth value, the controller 180 of the mobile terminal 300 can control the display unit 351 to output fourth data (e.g., text data and audio data for indicating that a user is currently in a state of having a high fever) different from the third data. The present embodiment is advantageous because a user of the mobile terminal 100 can be aware of a type and extent of a current state of a user of a mobile terminal 1400 by watching data output from the mobile terminal 1400.

Figure 20:
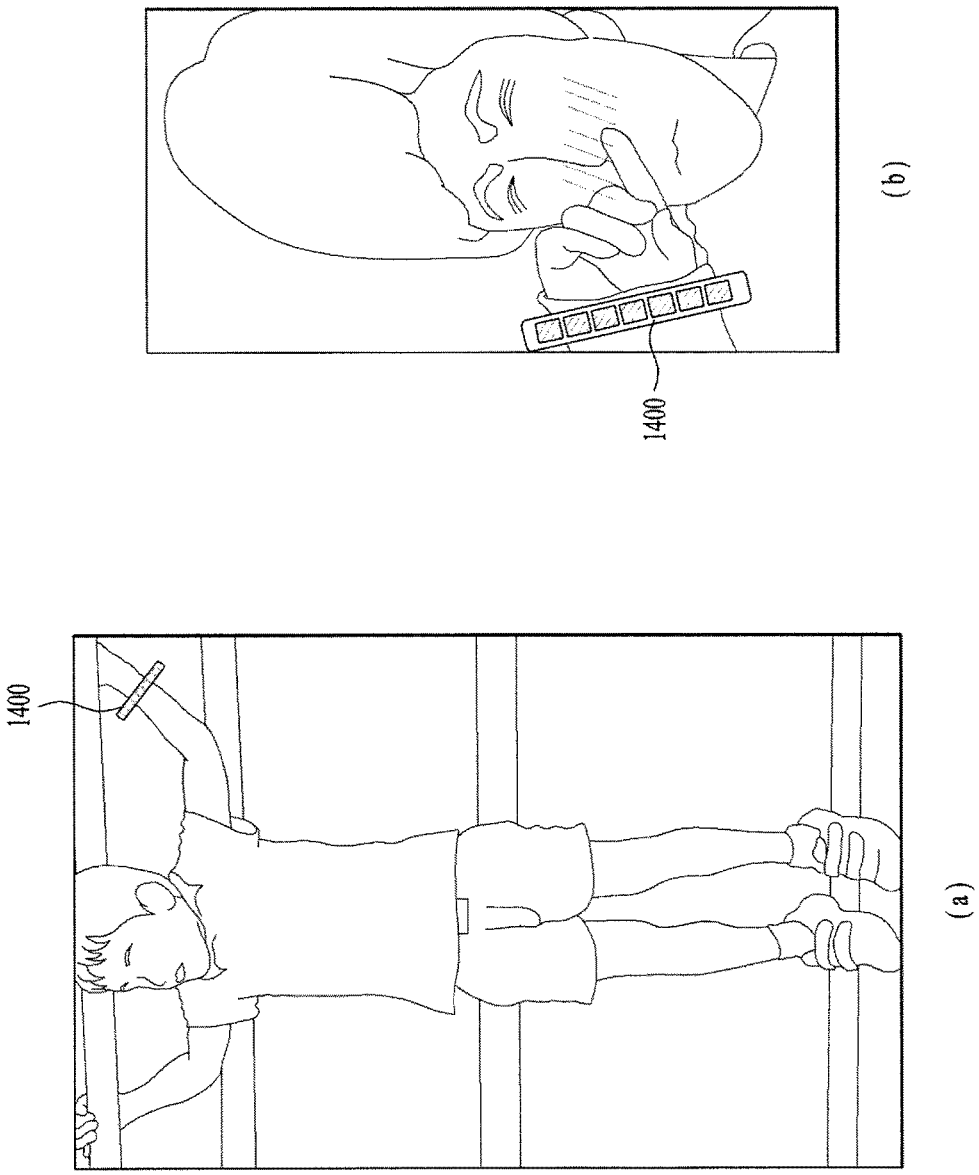
FIG. 20 is a diagram illustrating another example of a method of outputting a different data depending on a value of at least one of information on a surrounding environment and information on a user's state in a mobile terminal according to one embodiment of the present invention.

FIG. 20 is a diagram illustrating another example of a method of outputting a different data depending on a value of at least one of information on a surrounding environment and information on a user's state in a mobile terminal according to one embodiment of the present invention. Referring to FIG. 20 (a) and FIG. 20 (b), a mobile terminal 1400 may include one of a mobile terminal 300 of a watch type and a mobile terminal of a band type. Yet, the mobile terminal 1400 is non-limited by the mobile terminal 300 of the watch type or the mobile terminal of the band type and may further include one of a glass type terminal (e.g., a smart glass), an HMD (head mounted display), a headset and the like.

The controller 180 of the mobile terminal 1400 can control the sensing unit 140 to obtain at least one of first information on a surrounding environment and second information on a state of a user. If a value of at least one of the first information and the second information deviates from a range of a preset first value, the controller 180 can display the preset first data through the output unit 150. In this instance, the output unit 150 may include at least one of a display unit, an audio output unit, a haptic module and an optical output unit. And, the first data may include at least one of audio data, text data, optical data, video data, graphic data and vibration data.

Referring to FIG. 20 (a), if a value of specific information (e.g., information on a body temperature of a user) included in the second information is included in a range (e.g., a range of a value corresponding to a normal body temperature) of a preset first value, the controller 180 of the mobile terminal 1400 can deactivate the output unit. Referring to FIG. 20 (b), if a value of specific information (e.g., information on a body temperature of a user) included in the second information deviates from a range (e.g., a range of a value corresponding to a normal body temperature) of the preset first value, the controller 180 of the mobile terminal 1400 activates the deactivated output unit and can control the output unit to output first data (e.g., an optical data indicating a change of a body temperature, a text data indicating a change of a body temperature, etc.). According to an embodiment of the present invention, if such information on a user as a body temperature of a user deviates from a range of a normal value, it is advantageous in enabling the user to recognize the deviation.

Figure 21:
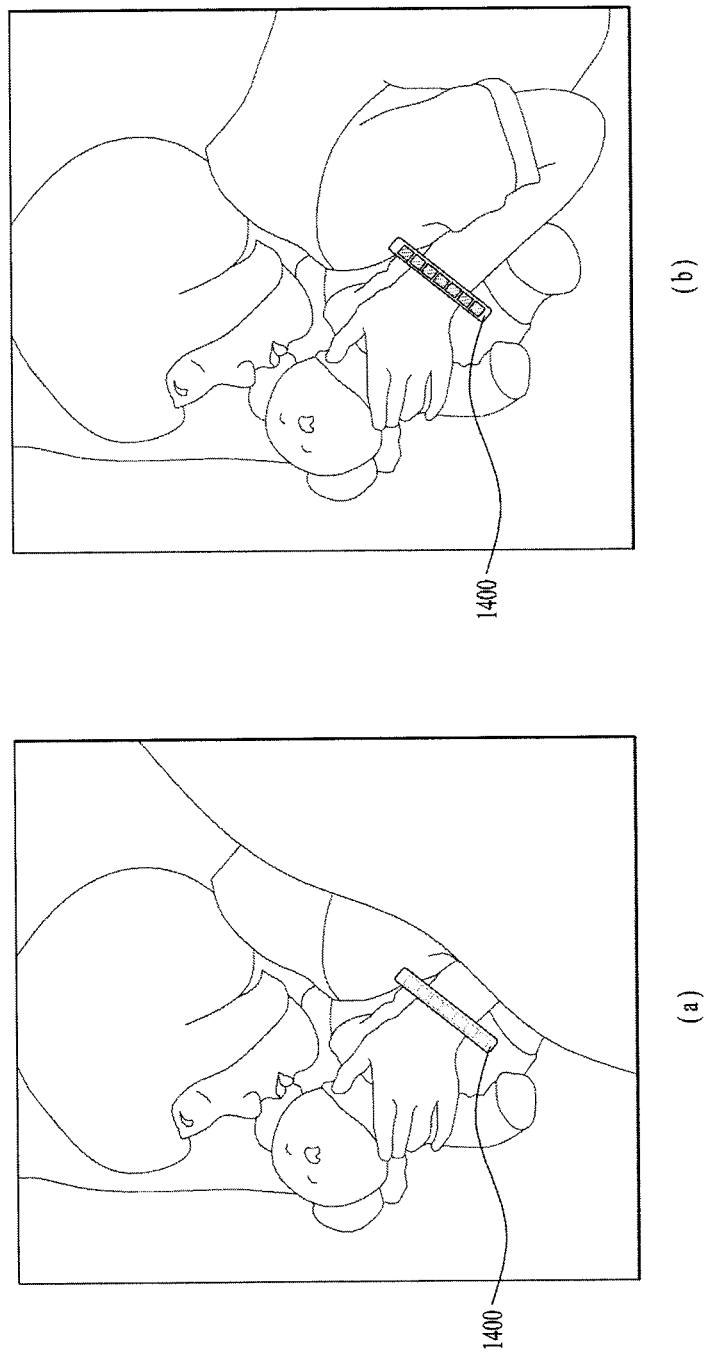
FIG. 21 is a diagram illustrating another example of a method of outputting a different data depending on a value of at least one of information on a surrounding environment and information on a user's state in a mobile terminal according to one embodiment of the present invention.

FIG. 21 is a diagram illustrating another example of a method of outputting a different data depending on a value of at least one of information on a surrounding environment and information on a user's state in a mobile terminal according to one embodiment of the present invention. Referring to FIG. 21, the controller 180 can control the sensing unit 140 to obtain at least one of first information on a surrounding environment and second information on a state of a user. If a value of at least one of the first information and the second information deviates from a range of a preset first value, the controller 180 can display a preset first data through the output unit 150. In this instance, the output unit 150 may include at least one of a display unit, an audio output unit, a haptic module and an optical output unit. And, the first data may include at least one of audio data, text data, optical data, video data, graphic data and vibration data.

Referring to FIG. 21 (a) and FIG. 21 (b), a mobile terminal 1400 may include one of a mobile terminal 300 of a watch type and a mobile terminal of a band type. However, the mobile terminal 1400 is non-limited by the mobile terminal 300 of the watch type or the mobile terminal of the band type and may further include one of a glass type terminal (e.g., a smart glass), an HMD (head mounted display), a headset and the like.

Referring to FIG. 21 (a), if a value of specific information (e.g., information on respiration of a user) included in the second information is included in a range (e.g., a range of a value corresponding to respiration of a sleeping user) of a preset first value, the controller 180 of the mobile terminal 1400 can switch the mobile terminal 1400 to a low power mode. For instance, the low power mode may mean a mode of minimizing a battery consumption of the power supply unit 190 by deactivating the output unit of the mobile terminal 1400.

However, if specific information (e.g., information on a body temperature of a user) included in the second information deviates from a range (e.g., a range of a value corresponding to a body temperature of a sleeping user covered with a blanket) of a preset first value, the controller 180 of the mobile terminal 1400 activates the output unit of the mobile terminal 1400 and can control the output unit to output first data (e.g., an optical data indicating that the user is not covered with the blanket or a text data indicating that a user is sleeping without being covered with a blanket). Thus, it can induce a person other than the user of the mobile terminal 1400 to cover the user of the mobile terminal 1400 with the blanket by checking the output first data.

According to an embodiment, if a value of at least one of the first information and the second information deviates from a range of a preset first value, the controller 180 can control the wireless communication unit 110 to transmit a specific signal to a preset external device. For instance, if specific information (e.g., information on a body temperature of a user) included in the second information deviates from a range (e.g., a range of a value corresponding to a body temperature of a sleeping user covered with a blanket) of a preset first value, the controller 180 can control the wireless communication unit 110 to transmit a signal, which indicates a state that the user is sleeping without being covered with the blanket, to a preset external device. Thus, if a user of the mobile terminal 1400 is sleeping without being covered with a blanket, it can induce the user of the preset external device to cover themselves with the blanket.

According to an embodiment of the present invention, if a user of the mobile terminal 1400 is sleeping without being covered with a blanket, a user of the mobile terminal 100 is provided with information on a user of the mobile terminal 1400. Therefore, it is advantageous in inducing the user of the mobile terminal 100 to cover themselves with the blanket.

FIG. 22 is a diagram illustrating another example of a method of outputting a different data depending on a value of at least one of information on a surrounding environment and information on a user's state in a mobile terminal according to one embodiment of the present invention. Referring to FIG. 22, the controller 180 can control the sensing unit 140 to obtain at least one of first information on a surrounding environment and second information on a state of a user.

If a value of at least one of the first information and the second information deviates from a range of a preset first value, the controller 180 can display a preset first data through the output unit 150. In this instance, the output unit 150 may include at least one of a display unit, an audio output unit, a haptic module and an optical output unit. And, the first data may include at least one of audio data, text data, optical data, video data, graphic data and vibration data.

For instance, referring to FIG. 22 (*a*), if a value of at least one of specific information (e.g., information on a surrounding temperature) included in the first information and specific information (e.g., information on a body temperature of a user) included in the second information deviates from a range (e.g., a range of a temperature value for a user not to catch a cold, a range of a value corresponding to a normal body temperature) of a preset first value, the controller 180 can control the display unit 351 to output a preset first data (e.g., a text data indicating that a user body needs to be warmed).

Meanwhile, if a value of at least one of the first information and the second information is included in a range of a preset second value, the controller 180 controls the output unit to output second data different from the first data and can also control the wireless communication unit 110 to transmit a specific signal to a preset external device. In this instance, the second data may include at least one of audio data, text data, optical data, video data, graphic data and vibration data.

For instance, referring to FIG. 22 (*b*), if a value of at least one of the first information and the second information corresponds to a range of a value corresponding to a situation that a user stays in a room over a preset period (e.g., 1 week), the controller 180 controls the wireless communication unit 110 to transmit a signal, which includes a message indicating that the user does not go out to an outdoor place, to a preset external device and can also control the display unit 351 to output second data (e.g., a text data for inducing a going-out) different from the first data.

In another instance, referring to FIG. 22 (*c*), if a value of at least one of the first information and the second information corresponds to a range of a value corresponding to a situation of an emergency, the controller 180 controls the wireless communication unit 110 to transmit a specific signal (e.g., a signal including audio data of recording surrounding sound) to a preset external device and can also control the display unit 351 to output second data (e.g., text data and vibration data for inducing a transmission of an outgoing call signal to a preset external device) different from the first data.

Figure 23:
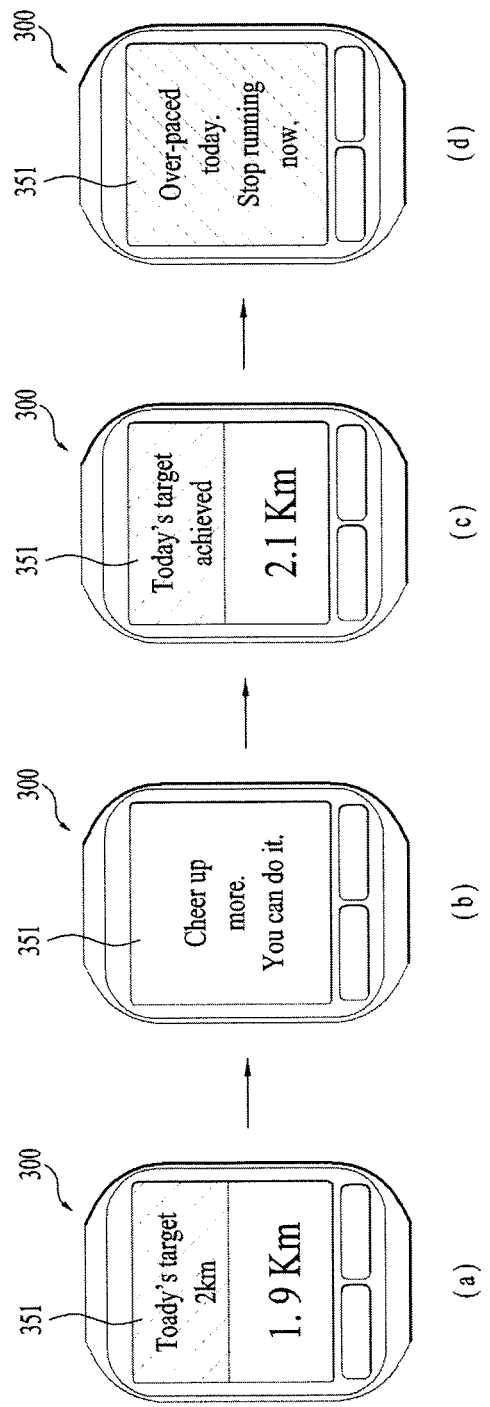
FIG. 23 is a diagram illustrating another example of a method of outputting a different data depending on a value of at least one of information on a surrounding environment and information on a user's state in a mobile terminal according to one embodiment of the present invention.

Meanwhile, according to an embodiment of the present invention, when a user does an exercise, the controller 180 recognizes an exercise amount and can output a message having a different content in accordance with the exercise amount. This is described in detail with reference to FIG. 23 as follows. In particular, FIG. 23 is a diagram illustrating another example of a method of outputting a different data depending on a value of at least one of information on a surrounding environment and information on a user's state in a mobile terminal according to one embodiment of the present invention. As shown, the controller 180 can control the sensing unit 140 to obtain at least one of first information on a surrounding environment and second information on a state of a user.

Referring to FIG. 23 (*a*), if a value of at least one of the first information and the second information corresponds to a range of a value corresponding to a situation that a user goes to running, the controller 180 can control the display unit 351 to output at least one of a text data indicating information on a user's target exercise amount previously saved in the memory 170 and a text data indicating information on a current exercise amount of the user.

Referring to FIG. 23 (*b*), if a value of at least one of the first information and the second information approaches a value of information on a user's target exercise amount previously saved in the memory 170, the controller 180 can control the display unit 351 to output a cheering message. According to an embodiment, if the controller 180 receives a specific signal (e.g., a signal including a cheering message, etc.) from a preset external device, the controller 180 can control the display unit 351 to output a preset second data (e.g., a cheering message included in the signal, a cheering message previously saved in the memory 170, etc.).

Referring to FIG. 23 (*c*), if a value of at least one of the first information and the second information deviates from a value of information on a user's target exercise amount previously saved in the memory 170, the controller 180 can control the display unit 351 to output at least one of a text data indicating that a target exercise amount is achieved and a text data indicating information on a current exercise amount of a user. Referring to FIG. 23 (*d*), if a value of at least one of the first information and the second information is included in a range of a value corresponding to a case that a user previously saved in the memory 170 exercises excessively, the controller 180 can control the display unit 351 to output a text data having a content indicating that 'stop exercising'.

According to the present embodiment, as the controller 180 outputs data in accordance with a user's exercise amount, it is advantageous in enabling a user of a mobile terminal 1400 to take exercise regularly. Further, it is also advantageous in preventing a user from taking exercise excessively.

Figure 24:
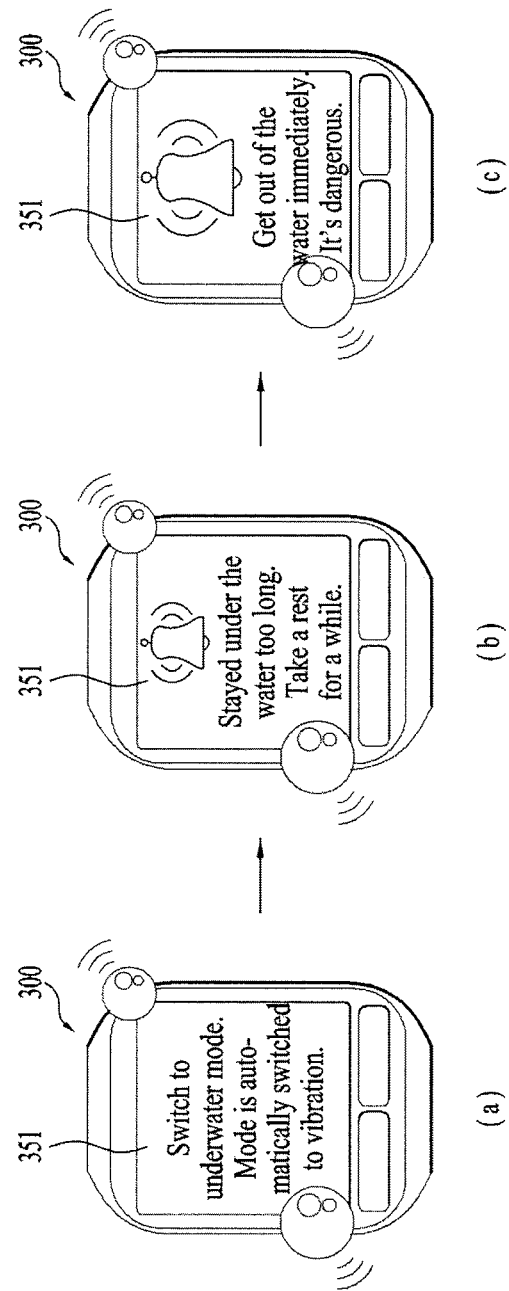
FIG. 24 is a diagram illustrating further example of a method of outputting a different data depending on a value of at least one of information on a surrounding environment and information on a user's state in a mobile terminal according to one embodiment of the present invention.

FIG. 24 is a diagram illustrating further example of a method of outputting a different data depending on a value of at least one of information on a surrounding environment and information on a user's state in a mobile terminal according to one embodiment of the present invention. Referring to FIG. 24, the controller 180 can control the sensing unit 140 to obtain at least one of first information on a surrounding environment and second information on a state of a user.

Referring to FIG. 24 (*a*), if a value of at least one of the first information and the second information corresponds to a range of a value corresponding to a state that a user is under the water, the controller 180 can switch the mobile terminal 300 to an underwater mode. For example, the underwater mode may mean a mode for a user under the water to recognize that a specific data is currently output by outputting vibration data as well in case of outputting the specific data through an output unit. Hence, although a user is under the water, the user can recognize that data is currently output from an output unit of a mobile terminal through the vibration data. In another example, the underwater mode may mean a mode for deactivating a function of a touchscreen of the display unit 351 or a mode for switching a touch input detection system of the touchscreen of the display unit 351.

Referring to FIG. 24 (*b*), if a value of at least one of the first information and the second information corresponds to a range of a value corresponding to a state that a user is under the water over a preset time (e.g., 1 hour), the controller 180 can control the display unit 351 to output a text data for inducing the user to take a rest. Further, the controller 180 can control the output unit to output the text data together with vibration data. Referring to FIG. 24 (*c*), if the controller 180 receives a specific signal (e.g., a signal for instructing to get out of water) from a preset external device, the controller 180 can control the display unit 351 to output a preset second data (e.g., a text data for instructing to get out of water immediately). Further, the controller 180 can control the output unit to output the text data together with vibration data.

Figure 25:
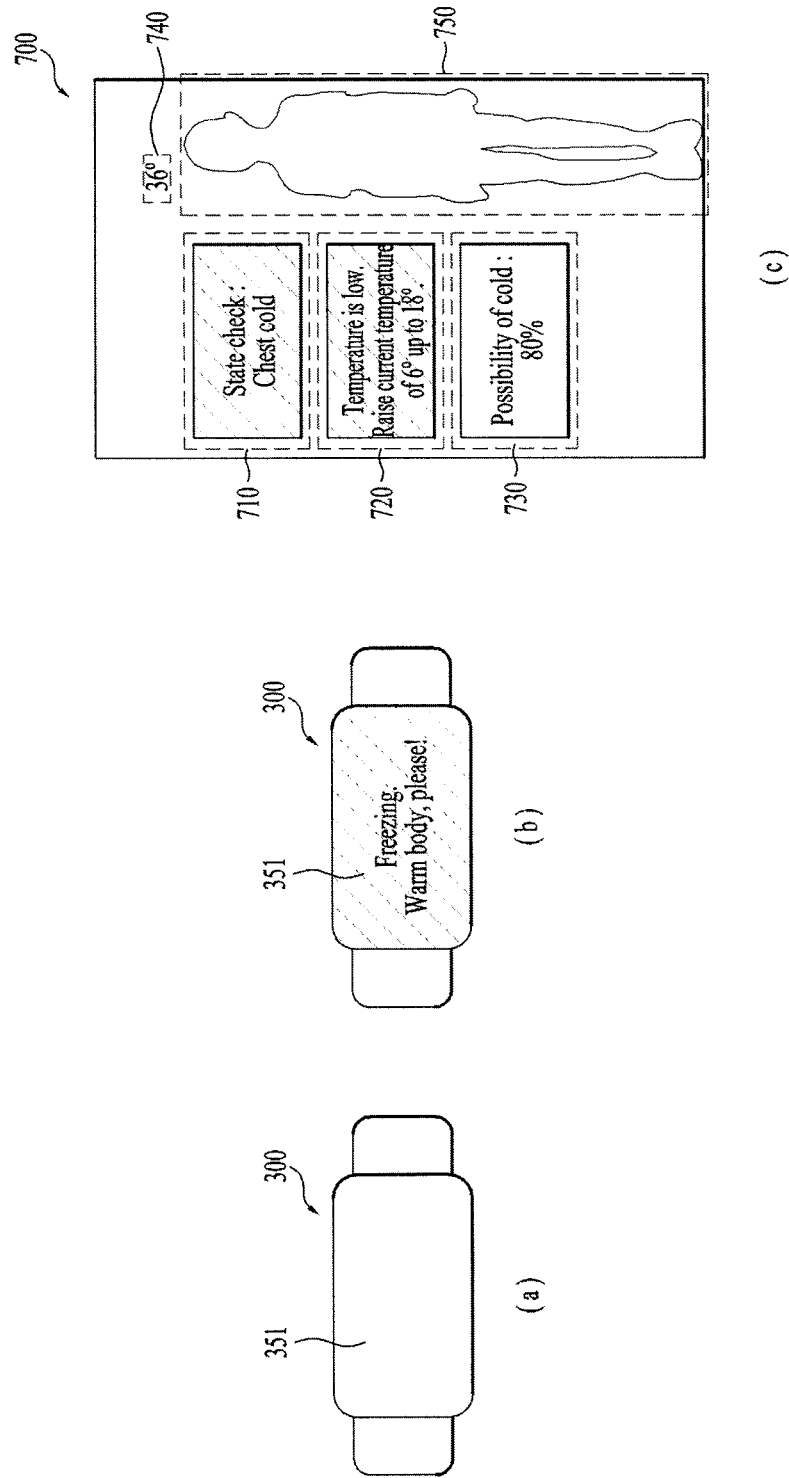
FIG. 25 is a diagram illustrating one example of a method of outputting various kinds of information through an output unit in a mobile terminal according to one embodiment of the present invention.

FIG. 25 is a diagram illustrating one example of a method of outputting various kinds of information through an output unit in a mobile terminal according to one embodiment of the present invention. Referring to FIG. 25, a mobile terminal shown in FIG. 25 (*a*) and FIG. 25 (*b*) is a first mobile terminal of a wearable type. The mobile terminal obtains at least one of first information on a surrounding environment and second information on a state of a user.

The mobile terminal transmits the obtained first and second information to a preset external device. If a value of at least one of the first information and the second information is included in or deviates from a range of a specific value, the mobile terminal can output specific data. In this instance, the first mobile terminal may include the mobile terminal 300 of the watch type described with reference to FIG. 3 or a mobile terminal of a band type. Yet, for clarity of the following description, assume that the first mobile terminal may include a mobile terminal of a watch type.

A second mobile terminal shown in FIG. 25 (*c*) may include a mobile terminal configured to receive the first information and the second information from the first mobile terminal 300 of the wearable type and to provide a user with various kinds of information. Referring to FIG. 25 (*a*), if a value of at least one of the first information and the second information is included in a range (e.g., a range of a value corresponding to a normal state) of a specific value, the controller 180 of the first mobile terminal 300 of the wearable type can deactivate the output unit.

Referring to FIG. 25 (*b*), if a value of at least one of the first information and the second information deviates from a range (e.g., a range of a value corresponding to a surrounding temperature for a user not to catch a cold) of a preset first value, the controller 180 of the first mobile terminal 300 of the wearable type activates the output unit and can then control the output unit (e.g., the display unit 351) to output a preset first data (e.g., a text data containing a content for inducing an increase of a surrounding temperature).

Moreover, if a value of at least one of the first information and the second information is included in a range (e.g., a range of a value corresponding to an emergency) of a preset second value, the controller 180 of the first mobile terminal 300 of the wearable type activates the output unit and can then control the output unit (e.g., the display unit 351) to output a preset second data (e.g., a text data indicating the emergency). Further, the controller 180 of the first mobile terminal 300 of the wearable type may control the wireless communication unit 110 to transmit a specific signal (e.g., a signal indicating the emergency) to a preset external device.

The controller 180 of the second mobile terminal 100 can receive at least one of the first information and the second information from the first mobile terminal 300 of the wearable type. The controller 180 of the second mobile terminal 100 can recognize a current state of a user of the first mobile terminal 300 of the wearable type using the first information, the second information and information (e.g., information on a disease history of the user of the first mobile terminal 300, information on a preset disease, etc.) saved in the memory. And, the controller 180 can extract a cause of the current state using the first information, the second information and the information saved in the memory.

Referring to FIG. 25 (*c*), if the controller 180 of the second mobile terminal detects a command for executing a child management application, the controller 180 of the second mobile terminal can output an executing screen 700 of the application. In this instance, the executing screen 700 includes at least one of a first region 710 related to an output of a current state of the user of the first mobile terminal 300, a second region 720 for outputting a different message depending on a cause of the current state of the user of the first mobile terminal 300, a third region 730 related to an output of a value of a probability that the user of the first mobile terminal 300 catches a specific disease (e.g., a cold, etc.), a fourth region 740 related to an output of the second information, and a fifth region 750 containing an image indicating the current state of the user of the first mobile terminal 300.

The controller 180 of the second mobile terminal may change a content of a message output to the first region 710 or an image included in the fifth region 750, depending on the recognized current state of the user of the first mobile terminal 300. For instance, if the current state of the user of the first mobile terminal 300 corresponds to a chest cold occurring state, the controller 180 of the second mobile terminal outputs a message 'Chest cold' to the first region 710 and can change the image included in the fifth region 750 into an image related to the chest cold. Further, the controller 180 can change an existing color of the first region 720 into a color different from the existing color.

The controller 180 of the second mobile terminal can output a message, which is different in accordance with the cause of the current state of the user of the first mobile terminal 300, to the second region 720. For instance, if the current state of the user of the first mobile terminal 300 corresponds to a chest cold caught state, the controller 180 of the second mobile terminal may output a message, which is provided to recover a user from the chest cold, to the second region 720. In particular, if the cause of the chest cold is extracted as a low temperature, the controller 180 can display a message (e.g., a message instructing to increase 6 degrees of a current temperature up to 18 degrees) for inducing a removal of the cause of the chest cold to the second region 720.

The controller 180 of the second mobile terminal can output a value of probability that the user of the first mobile terminal 300 catches a specific disease (e.g., a cold) to the third region 730. The controller 180 of the second mobile terminal can output specific information (e.g., information on a body temperature of the user of the first mobile terminal 300) included in the second information to the fourth region 740.

An embodiment of the present invention is advantageous in that information related to a current state is provided to the user of the first mobile terminal 300 of the wearable type.

And, it is also advantageous in that a current state of the user of the first mobile terminal and the cause of the current state can be provided to a user of the second mobile terminal connected to the first mobile terminal 300 by wireless communication.

According to the above-described embodiments of the present invention, a user's current state of a preset external device can be easily removed by recognizing the user's current state of the preset external device and then extracting a cause of the recognized current state. Moreover, an occurrence of a cause of deterioration of health is detected in advance before user's health of a preset external device deteriorates, whereby the detected cause can be removed beforehand.

A mobile terminal and method for controlling the same according to an embodiment of the present invention provide the following effects and/or features. According to at least one of embodiments of the present invention, a user's current state of a preset external device can be easily removed by recognizing the user's current state of the preset external device and then extracting a cause of the recognized current state. According to at least one of embodiments of the present invention, an occurrence of a cause of deterioration of health is detected in advance before user's health of a preset external device deteriorates, whereby the detected cause can be removed beforehand.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal. The controller includes a sufficient structure such as a hardware-embedded processing chip having the appropriate algorithms to perform the described functions.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A mobile terminal, comprising:
a memory configured to store at least one of first information on a disease history of a preset user and second information on a preset disease;
a wireless communication unit configured to receive information obtained through a sensor of a preset wearable device, wherein the received information comprises at least one of third information obtained from sensing a surrounding environment of the preset wearable device and fourth information obtained from sensing a current state of the preset user;
a display unit; and
a controller configured to:
determine a health-related state of the preset user using the first information, the second information, the third information and the fourth information,
control the display unit to output information about a predicted health-related state of the preset user, including a probability value of catching a specific disease, using the health-related state of the preset user, wherein the probability value of catching the specific disease is a numerical value indicating an extent that a value included in at least one of the third information and fourth information corresponds to a value included in at least one of the first information and second information,
in response to the specific disease being predicted:
determine a cause of the specific disease based on the health-related state of the preset user,
output information on the display unit regarding the determined cause of the specific disease of the preset user, and
output a message on the display unit on how to remove the cause of the specific disease of the preset user,
control the wireless communication unit to re-receive the third information and the fourth information from the preset wearable device, in response to a preset time expiring after displaying the message,
determine whether or not the cause of the specific disease of the preset user is removed based on the re-received third information and the re-received fourth information, and
if the cause is removed, determine whether the health-related state of the preset user has been changed after a preset time has elapsed and save a cause of the detected change of the health-related state of the preset user as the first information in the memory,
wherein the first information includes at least one of a type of disease caught by the preset user, information on a specific life pattern corresponding to the disease caught by the preset user, information on the surrounding environment corresponding to the disease caught by the preset user, and information on a state of the preset user corresponding to the disease caught by the preset user.

2. The mobile terminal of claim 1, wherein the controller is further configured to: to determine fifth information on a life pattern of the preset user using at least one of the first information and the received information.

3. The mobile terminal of claim 1, further comprising:
an output unit configured to output at least one of audio data, text data, optical data, video data, graphic data, and vibration data if the health-related state of the preset user corresponds to a preset specific situation.

4. The mobile terminal of claim 1, wherein the controller is further configured to control the wireless communication unit to transmit a specific signal to the preset wearable device if the health-related state of the preset user corresponds to a preset specific situation.

5. The mobile terminal of claim 1, wherein the fourth information includes at least two of information on a respiration of the preset user, information on a motion of the preset user, information on a heart rate of the preset user, information on a body temperature of the preset user, and information on a skin temperature of the preset user.

6. The mobile terminal of claim 1, wherein the controller is configured to output on the display unit a first region, and second region, a third region, a fourth region, and a fifth region,
- wherein the first region includes the health-related state of the preset user,
- wherein the second region includes information regarding the cause of the specific disease,
- wherein the third region includes the probability value,
- wherein the fourth region includes a body temperature of the preset user, and
- wherein the fifth region includes an image indicating the health-related state of the preset user.

7. The mobile terminal of claim 6, wherein in response to the probability value being equal to or greater than 50%, the controller is configured to change an output color of the third region.

8. A method of controlling a mobile terminal, the method comprising:
- storing, via a memory associated with the mobile terminal, at least one of first information on a disease history of a preset user and second information on a preset disease;
- receiving, via a wireless communication unit of the mobile terminal, information obtained through a sensor of a preset wearable device, wherein the received information comprises at least one of third information obtained from sensing a surrounding environment of the preset wearable device and fourth information obtained from sensing a current state of the preset user;
- determining, via a controller of the mobile terminal, a health-related state of the preset user using the first information, the second information and the received information;
- outputting, via a display unit of the mobile terminal, information about a predicted health-related state of the preset user, including a probability value of catching a specific disease, wherein the probability value of catching the specific disease is a numerical value indicating an extent that a value included in at least one of the third information and fourth information corresponds to a value included in at least one of the first information and second information,
- in response to the specific disease being predicted:
  - determining a cause of the specific disease based on the health-related state of the preset user,
  - outputting, via the display unit, information about the determined cause of the specific disease of the preset user, and
  - outputting, via the display unit, a message on how to remove the specific disease of the preset user;
- re-receiving, via the wireless communication unit, the third information and the fourth information from the preset wearable device, in response to a preset time expiring after displaying the message;
- determining, via the controller, whether or not the cause of the specific disease is removed based on the re-received third information and the re-received fourth information;
- if the extracted cause is not removed, re-displaying, via the display unit, the message on how to remove the cause of the specific disease of the preset user on the display unit; and
- if the cause is removed, determining, via the controller, whether the health-related state of the preset user has been changed after a preset time has elapsed and save a cause of the detected change of the health-related state of the preset user as the first information in the memory,
- wherein the first information includes at least one of a type of a disease, a specific life pattern, information on a surrounding environment, and information on a state of the preset user corresponding to the disease caught by the preset user.

9. The method of claim 8, further comprising:
determining fifth information on a life pattern of the preset user using at least one of the first information and the received information.

10. The method of claim 8, further comprising:
outputting, via an output unit of the mobile terminal, at least one of audio data, text data, optical data, video data, graphic data, and vibration data if the health-related state of the preset user corresponds to a preset specific situation.

11. The method of claim 8, further comprising:
transmitting, via the wireless communication unit, a specific signal to the preset wearable device if the health-related state of the preset user corresponds to a preset specific situation.

12. The method of claim 8, wherein the fourth information includes at least two of information on a respiration of the preset user, information on a motion of the preset user, information on a heart rate of the preset user, information on a body temperature of the preset user, and information on a skin temperature of the preset user.

13. The method of claim 8, wherein the controller outputs on the display unit a first region, and second region, a third region, a fourth region, and a fifth region,
- wherein the first region includes the health-related state of the preset user,
- wherein the second region includes information regarding the cause of the specific disease,
- wherein the third region includes the probability value,
- wherein the fourth region includes a body temperature of the preset user, and
- wherein the fifth region includes an image indicating the health-related state of the preset user.

14. The method of claim 13, wherein in response to the probability value being equal to or greater than 50%, the controller changes an output color of the third region.

* * * * *